(12) United States Patent
Bonander

(10) Patent No.: US 10,385,309 B2
(45) Date of Patent: Aug. 20, 2019

(54) *SACCHAROMYCES CEREVISIAE* STRAINS

(71) Applicant: SCANDINAVIAN TECHNOLOGY GROUP AB, Lund (SE)

(72) Inventor: Nicklas Bonander, Mölndal (SE)

(73) Assignee: SCANDINAVIAN TECHNOLOGY GROUP AB, Lund (SE)

( * ) Notice: Subject to any disclaimer, the term of this patent is extended or adjusted under 35 U.S.C. 154(b) by 68 days.

(21) Appl. No.: 15/305,480

(22) PCT Filed: Apr. 23, 2015

(86) PCT No.: PCT/SE2015/050456
§ 371 (c)(1),
(2) Date: Oct. 20, 2016

(87) PCT Pub. No.: WO2015/163814
PCT Pub. Date: Oct. 29, 2015

(65) Prior Publication Data
US 2017/0037361 A1    Feb. 9, 2017

(30) Foreign Application Priority Data

Apr. 23, 2014 (SE) ....................... 1450484
Jul. 4, 2014 (SE) ....................... 1450851

(51) Int. Cl.
*C12R 1/865* (2006.01)
*C12N 1/18* (2006.01)
*C12N 9/04* (2006.01)
*C12N 9/12* (2006.01)
*C12P 7/10* (2006.01)

(52) U.S. Cl.
CPC .............. *C12N 1/18* (2013.01); *C12N 9/0006* (2013.01); *C12N 9/1205* (2013.01); *C12P 7/10* (2013.01); *C12R 1/865* (2013.01); *C12Y 101/01009* (2013.01); *C12Y 101/01307* (2013.01); *C12Y 207/01017* (2013.01); *Y02E 50/16* (2013.01); *Y02E 50/17* (2013.01)

(58) Field of Classification Search
CPC .. C12P 7/10; C12R 1/865; C12N 1/18; C12N 9/0006; C12N 9/1205; Y02E 50/16; Y02E 50/17; C12Y 101/01009; C12Y 101/01307; C12Y 207/01017
See application file for complete search history.

(56) References Cited

FOREIGN PATENT DOCUMENTS

| WO | 2005121337 A1 | 12/2005 |
| WO | 2006115455 A1 | 11/2006 |
| WO | 2009155633 A1 | 12/2009 |

OTHER PUBLICATIONS

Toivari et al., Applied and Environmental Microbiology 70(6):3681-3686, 2004.*
PCT International Search Report dated Jul. 16, 2015 from corresponding Application No. PCT/SE2015/050456.

* cited by examiner

*Primary Examiner* — Delia M Ramirez
(74) *Attorney, Agent, or Firm* — Dilworth IP, LLC

(57) ABSTRACT

The present invention relates to a method of preparing a strain of sugar fermenting *Saccharomyces cerevisiae* with capability to ferment xylose, wherein said method comprises different procedural steps. The method comprises mating a first sporulated *Saccharomyces cerevisiae* strain with a second *Saccharomyces cerevisiae* haploid strain. Thereafter, screening for mated cells is performed, growing such mated cells, and verifying that mated cells exhibit basic morphology by microscopic inspection. Thereafter, creation of a mixture of the mated cells is performed, subjecting the mixture to continuous chemostat lignocellulose cultivation and obtaining the sugar fermenting *Saccharomyces cerevisiae* cells with capability to ferment xylose is performed. The invention also comprises strains obtained by said method.

1 Claim, 15 Drawing Sheets
Specification includes a Sequence Listing.

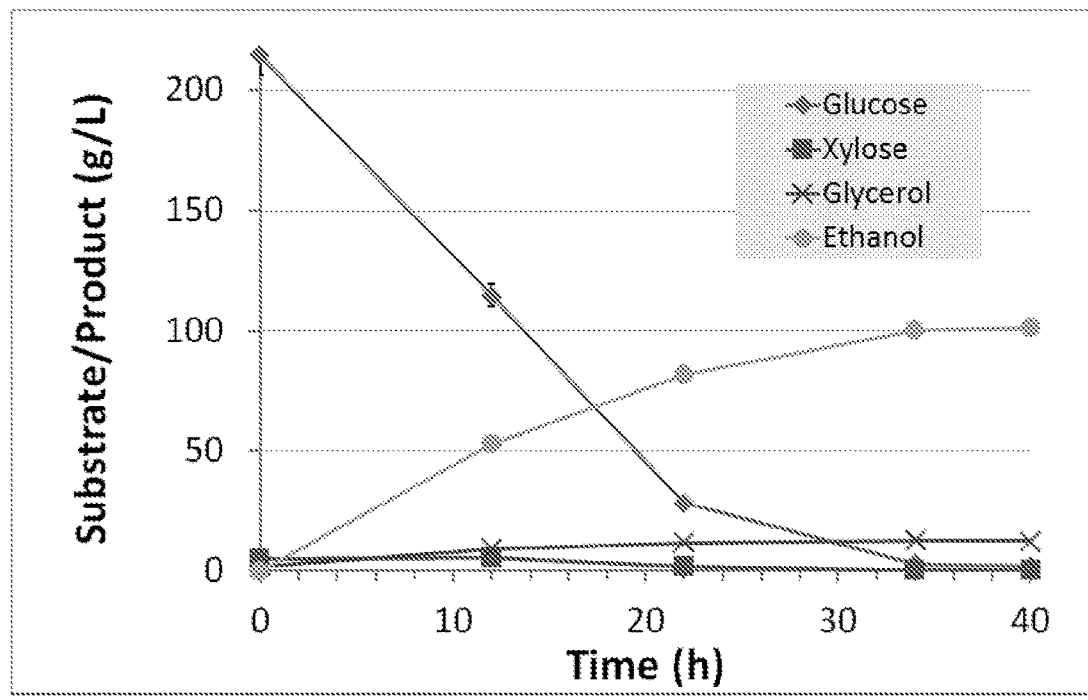

Figure 23

MSSIKLNSGYDMPQVGFGCWKSTTTCADQIYNAIKVGYRLFDGAEDYGNEKEVGDGIK
RAIDEGLVARDELFVVSKLWNNFHHPDNVEKALDRTLSDLKVDYLDLFLIHFPIAFKF
VPFDEKYPPGFYCGDGDKFIYEDVPLLSTWKKLEEMVKKGKVRSIGISNFCGGLIQDL
LRGAEIPPAVLQIEHHPYLQQPRLVKWVQSKGIA<u>ITAYSSF</u>GT<u>QSFVELD</u>IPKVDNCV
TLFKHEDIVSIAENHKKSTA<u>QVLLRW</u>ATQRGLAV<u>IPKSNQTERLVANLTVN</u>DFDLTNE
EIETISKLDINLRFNDPWDWDKIPIFV

| Medium | Figure/strain | Glucose | Xylose | TS[1] | $Y^2_{EtOH}/TS$ | $Y^3_{xylitol}/cons.xylose$ | $Y_{glycerol}/TS$ | HAc | HMF | Furfural |
|---|---|---|---|---|---|---|---|---|---|---|
| Wheat straw | 4 / T13 | 6 | 30 | 36 | 0,51 | 0,02 | 0,03 | 2,6 | 0,1 | 2 |
| Bagasse | 5/ T13 | 6 | 12 | 16 | 0,51 | 0,02 | 0,04 | 9,5 | 0,1 | 1,8 |
| Birch | 6/ T13 | 7 | 46 | 53 | 0,51 | 0,01 | 0,02 | 9,5 | 0,1 | 1,6 |
| Corn stover | 7/ T13 | 60 | 27 | 87 | 0,51 | 0,01 | 0,08 | 0,9 | 0,1 | n.d. |
| Hard wood | 8/ T13 | 21 | 10 | 31 | 0,5 | 0,02 | 0,04 | 2,1 | 0,06 | n.d. |
| SSF wheat straw | 9/ T13 | 22 | 45 | 67 | 0,5 | <,01 | <,01 | 1,2 | 0,08 | 1,5 |
| SSF corn cobs | 10/ T13 | 11 | 57 | 68 | 0,5 | <,01 | <,01 | 3,5 | 0,08 | 1,4 |
| corn stoverfed-batch | 11/ T13 | 108 | 0 | 108 | 0,45 | 0,01 | 0,08 | 1,7 | 0,2 | n.d. |
| Minimal medium | 12/ T13 | 106 | 71 | 177 | 0,44 | 0,01 | 0,01 | 8 | 0 | 0 |
| Minimal medium | 13/ T14 | 66 | 16 | 82 | 0,4 | <0,01 | 0,02 | 1,2 | 0 | 0 |
| Minimal medium | 14/ T15 | 66 | 16 | 82 | 0,39 | <0,01 | 0,02 | 1,2 | 0 | 0 |
| Minimal medium | 15/ T16 | 66 | 16 | 82 | 0,41 | <0,01 | 0,02 | 1,2 | 0 | 0 |
| Minimal medium | 16/ T17 | 66 | 16 | 82 | 0,37 | <0,01 | 0,02 | 1,2 | 0 | 0 |
| Corn stover | 17/ T14 | 94 | 40 | 134 | 0,4 | <0,01 | 0,02 | 1,2 | 0,1 | n.d. |
| Corn stover | 18/ T15 | 94 | 40 | 134 | 0,4 | <0,01 | 0,02 | 1,2 | 0,1 | n.d. |
| Corn stover | 19/ T16 | 94 | 40 | 134 | 0,41 | <0,01 | 0,02 | 1,2 | 0,1 | n.d. |
| Corn stover | 20/ T17 | 94 | 40 | 134 | 0,39 | <0,01 | 0,02 | 1,2 | 0,1 | n.d. |
| Corn cobs | 21/ T13 | 128 | 88 | 216 | 0,49 | <0,01 | 0,02 | 3,2 | 0,6 | 1,5 |
| Bagasse | 22/ T13 | 124 | 85 | 209 | 0,49 | <0,01 | 0,015 | 2,0 | 0,3 | 1,2 |
| Corn mash | 23/T13 | 215 | 6 | 221 | 0,46 | <0,01 | 0,06 | >0,5 | 0 | 0 |

SEQUENCE LISTING

```
<160> NUMBER OF SEQ ID NOS: 1

<210> SEQ ID NO 1
<211> LENGTH: 288
<212> TYPE: PRT
<213> ORGANISM: Saccharomyces cerevisiae

<400> SEQUENCE: 1

Met Pro Gln Val Gly Phe Gly Cys Trp Lys Ser Thr Thr Thr Cys Ala
1               5                   10                  15

Asp Gln Ile Tyr Asn Ala Ile Lys Val Gly Tyr Arg Leu Phe Asp Gly
            20                  25                  30

Ala Glu Asp Tyr Gly Asn Glu Lys Glu Val Gly Asp Gly Ile Lys Arg
        35                  40                  45

Ala Ile Asp Glu Gly Leu Val Ala Arg Asp Glu Leu Phe Val Val Ser
    50                  55                  60

Lys Leu Trp Asn Asn Phe His His Pro Asp Asn Val Glu Lys Ala Leu
65                  70                  75                  80

Asp Arg Thr Leu Ser Asp Leu Lys Val Asp Tyr Leu Asp Leu Phe Leu
                85                  90                  95

Ile His Phe Pro Ile Ala Phe Lys Phe Val Pro Phe Asp Glu Lys Tyr
            100                 105                 110

Pro Pro Gly Phe Tyr Cys Gly Asp Gly Asp Lys Phe Ile Tyr Glu Asp
        115                 120                 125

Val Pro Leu Leu Ser Thr Trp Lys Lys Leu Glu Glu Met Val Lys Lys
    130                 135                 140

Gly Lys Val Arg Ser Ile Gly Ile Ser Asn Phe Cys Gly Gly Leu Ile
145                 150                 155                 160

Gln Asp Leu Leu Arg Gly Ala Glu Ile Pro Pro Ala Val Leu Gln Ile
                165                 170                 175

Glu His His Pro Tyr Leu Gln Gln Pro Arg Leu Val Lys Trp Val Gln
            180                 185                 190

Ser Lys Gly Ile Ala Ile Thr Ala Tyr Ser Ser Phe Gly Pro Gln Ser
        195                 200                 205

Phe Val Glu Leu Asp His Pro Lys Val Asp Asn Cys Val Thr Leu Phe
    210                 215                 220
```

-continued

```
Lys His Glu Asp Ile Val Ser Ile Ala Glu Asn His Lys Lys Ser Thr
225                 230                 235                 240

Ala Gln Val Leu Leu Arg Trp Ala Thr Gln Arg Gly Leu Ala Val Ile
            245                 250                 255

Pro Lys Ser Asn Gln Thr Glu Arg Leu Val Ala Asn Leu Thr Val Asn
            260                 265                 270

Asp Phe Asp Leu Thr Asn Glu Glu Ile Glu Thr Ile Ser Lys Leu Asp
        275                 280                 285
```

SACCHAROMYCES CEREVISIAE STRAINS

TECHNICAL FIELD OF THE INVENTION

The present invention relates to a method of preparing a strain of sugar fermenting *Saccharomyces cerevisiae* with capability to ferment xylose, to *Saccharomyces cerevisiae* strains as obtained through said method and to the use of said prepared strains of the invention for fermentation of sugar containing biomass hydrolysates to ethanol.

BACKGROUND ART

Strains of the genus *Saccharomyces* are used widely in the industry for brewing, distilling, baking, bioethanol production and various other applications. *Saccharomyces cerevisiae* is one of the most widely used microorganisms in industrial applications in view of it's ability to convert sugars such as glucose, fructose, mannose, maltose and sucrose to cell mass, and fermenting these sugars to ethanol. Strains of *Saccharomyces cerevisiae* are used in the fuel industry in view of their ability to rapidly convert sugars into ethanol. *Saccharomyces cerevisiae* has a better tolerance towards fermentation inhibitors and ethanol compared to bacteria and other yeast species.

Unlike bacteria and several yeast species, wild-type *Saccharomyces cerevisiae* is not able to use pentoses such as xylose and arabinose as carbon source. The ability of *Saccharomyces cerevisiae* to grow on abundant carbon sources such as side streams and residual material from other processes, such as agricultural residual material from e.g. maize and bagasse, and residual material from e.g. paper manufacture, is of great environmental, but also economical, value. Agricultural residual material and hardwood derived streams comprise a rather large fraction of hemicellulose, which is built from many different sugar monomers. For instance, besides glucose, these sugar monomers can include xylose, mannose, galactose, rhamnose and arabinose. Glucose and xylose are the sugar monomers that are present in the largest amount and thus represents an important carbon source for the manufacturing of ethanol using yeasts, providing a huge economic and environmental advantage. The abundance of xylose in mentioned materials and the possibility to use yeasts, such as *Saccharomyces cerevisiae*, to produce ethanol using xylose as carbon source has led to intense research within this field of technology. The conversion of xylose has however sometimes been poor resulting in a poor ethanol production. Further the production of the byproduct xylitol has been rather large.

Genes encoding enzymes giving the ability to use xylose as carbon source have previously been introduced in *Saccharomyces cerevisiae*.

A comparison using a blast search of the amino acid sequences Xyl1 (xylose reductase) and Xyl2 (xylitol dehydrogenase) from *Scheffersomyces stipitis* with all proteins in *S. cerevisiae* show that the closest homologues are Gre3p (Sc) E-value: 3E-100 with Xyl1, and Xyl2 is closest to Sor1p, Sor2 E-value 1.4E-86 to 1E-77. The smaller the E value the larger homology of the genes. Thus, a large homology between sequences is observed. EP 1 282 686 discloses recombinant *Saccharomyces cerevisiae* strains having incorporated genes for the enzymes xylose reductase, xylitol dehydrogenase and xylulokinase as well as having been subjected to a specific mutation. Said strains have the ability to ferment lignocellulose raw materials to ethanol. The strain deposited in Ep 1 282 686 is CBS 102679 (TMB3400, Taurus01) is generally recognised to be efficient in the prior art. The ethanol produced by the strain CBS 102679 has been considered very good compared to other prior art recombinant yeasts, but there is also a production of the undesirable byproduct xylitol. Therefore, there is still a need within the art to provide new strains of *Saccharomyces cerevisiae* having an even better ethanol production, better xylose conversion as well as lower xylitol production.

WO2012/067572 discloses *Saccharomyces cerevisiae* strains Taurus03 with deposit number CBS128138, Taurus04 with deposit number CBS 128139, Taurus07 with deposit number CBS128140, Taurus10 with deposit number CBS128141, which all are xylose fermenting yeast strains producing beneficial ethanol yields.

The β-lactamase gene is included in at least the strains Taurus01, Taurus04 and Taurus07 as mentioned above. The authorities in the US do not allow the use of *Saccharomyces cerevisiae* strains, which contain the β-lactamase gene, in larger production facilities in view of risk for genetic transfer of the gene to another organism which then potentially can obtain antibiotic resistance.

There is still a need within the technical field to provide robust *Saccharomyces cerevisiae* strains providing high ethanol yields from both 5- and 6-carbon sugars and in addition exhibiting low by-product yields of eg xylitol. *Saccharomyces cerevisiae* strains not having the above mentioned β-lactamase gene in the genome are especially needed.

SUMMARY OF INVENTION

In view of the above, the present invention relates to efficient *Saccharomyces cerevisiae* strains that have been prepared by the method as described below. The strains prepared have reached ethanol yields during fermentation of sugars being close to the theoretical possible in view of the total amount of sugar present in the fermentation medium, eg a biomass hydrolysate.

The present invention relates, in one aspect, to a strain of *Saccharomyces cerevisiae* comprising at least one native XKS1 gene in its genome encoding xylulokinase, at least one native XDH1 gene in its genome encoding xylitol dehydrogenase, and at least one modGre3 gene in its genome, said modGre3 gene encoding an amino acid sequence of SEQ ID NO 1 having xylose reductase activity or encoding a fragment of said amino acid sequence having xylose reductase activity, wherein said strain is obtainable by the following steps:

a) sporulating a first strain of *Saccharomyces cerevisiae* for providing at least 20 tetrads of said strain,
b) introducing DNA, encoding for xylose reductase and xylitol dehydrogenase obtained from *Scheffersomyces stipitis* and xylulokinase obtained from *Saccharomyces cerevisiae*, into a second strain of *Saccharomyces cerevisiae*,
c) mating the first sporulated *Saccharomyces cerevisiae* strain with the second *Saccharomyces cerevisiae* strain evolved on xylose and in a haploid state by mixing cells of said *Saccharomyces cerevisiae* haploid strain with each tetrad obtained in step a) to provide mated cells on an YPD agar plate,
d) screening for mated cells on xylose and geneticin agar plates,
e) growing mated cells from step d) in minimal defined xylose liquid medium, f) verifying that the mated cells exhibit basic morphology features of budding yeast by microscopic inspection and selecting such mated cells with basic morphological features, g) creation of a mixture of the mated cells with basic morphology features in equal amounts from step f), h) subjecting the mixture to continuous chemostat cultivation firstly in a microaerobic environment and thereafter in a anaerobic environment using feeding strategy with defined xylose medium feed for at least 0.08 h$^{-1}$ in cyclus of feed and disrupted feed in a cyclus time range of a few hours, and thereafter with constant feed for at least 0.13 h$^{-1}$, i) subjecting the mixture to continuous chemostat cultivation in an anaerobic environment with cells from step h) using lignocellulose feeding with xylose medium for at least 0.08 h$^{-1}$ in cyclus of feed and disrupted feed in a cyclus time range of a few hours, and with constant feed rate for at least 0.13 h$^{-1}$, j) obtaining the sugar fermenting *Saccharomyces cerevisiae* cells with capability to ferment xylose by collecting said cells from the chemostat reactor, k) diluting the cells from chemostat into water, then plating cells onto YPD agar plate to obtain single colonies, and incubating at 30° C. for at least 4 days.

The present invention relates, in yet another aspect, to a strain that is Taurus 13 having deposition number CBS137333, Taurus 14 having deposition number CBS 137663, Taurus 15 having deposition number CBS 137664, Taurus 16 having deposition number CBS 137665, or Taurus 17 having deposition number CBS 137666.

The present invention relates, in yet another aspect, to the use of a strain of *Saccharomyces cerevisiae* obtainable as described above, for fermentation of sugar containing hydrolysates or biomass to ethanol.

BRIEF DESCRIPTION OF DRAWINGS

FIG. 24. Amino acid sequence of modGre3 (SEQ ID NO: 1). The strains of the invention with modGre3 have >5 times higher in vitro xyloses reductase activity compared with Gre3 containing USM21 (CBS102678). Bold amino acids are $NADP^+$ interacting and grey shaded amino acids are the two main polypeptide streches with conserved amino acids that interact with the nucleotide and that are important for catalysis in the folded 3D-structure.

FIG. 26 discloses table1 presenting concentrations of extra cellular substrate/product in g/L during anaerobic fermentation of hydrolysates and minimal medium, yields of ethanol, xylitol, glycerol. No other metabolite is accumlating in the medium. The g/L content of acetate (HAc), HMF (Hydroxymethylfurfural) and furfural at the beginning of the fermention are also shown. 1. TS=total sugar (g/L glucose+ g/L xylose); 2. Y is yield (g/g) of ethanol and glycerol from consumed glucose and xylose: ethanol, xylitol or glycerol; 3. Y is yield (g/g) of xylitol from consumed xylose; cons. Xylose=consumed xylose; cons. TS=consumed total sugar; n.d.=not detected~0-0.05 g/L.

DETAILED DESCRIPTION OF THE INVENTION

Figure 1:
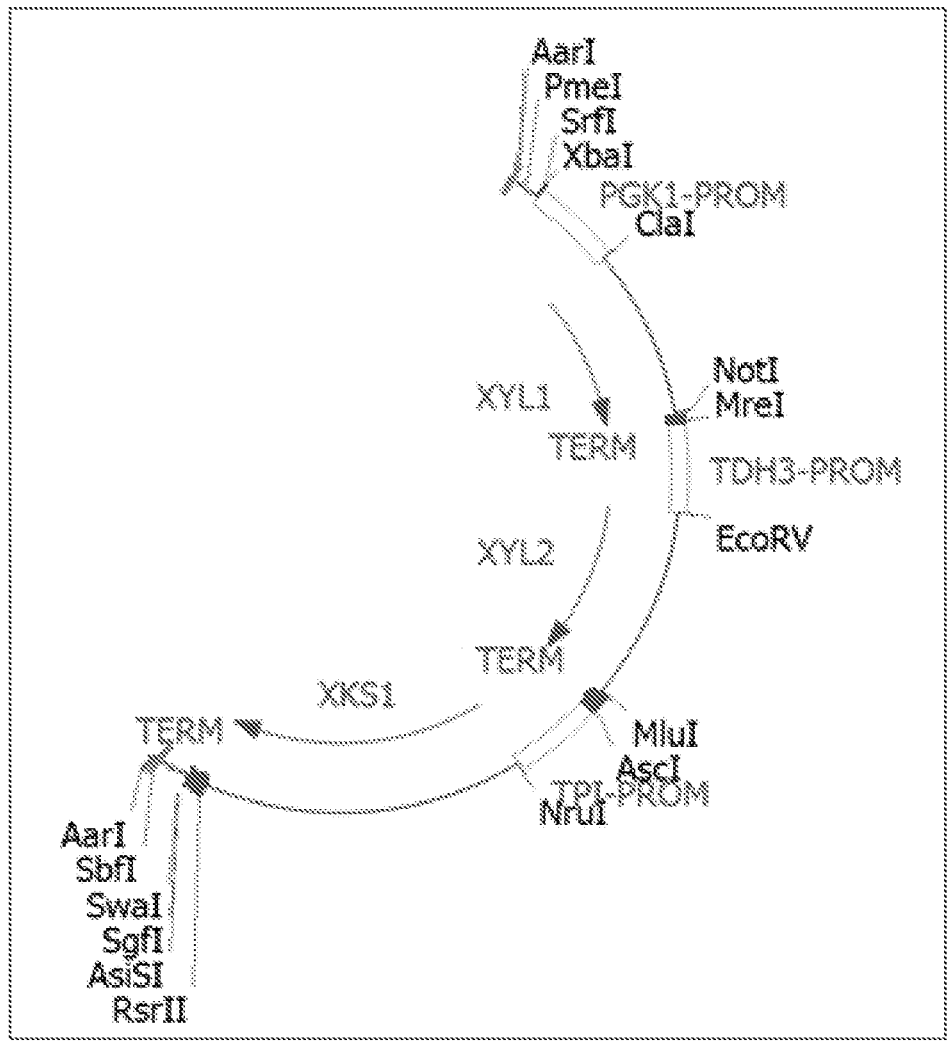
FIG. 1. Genetic element with the genes XYL1, XYL2 and XKS1 (red-arrows) used in genomic integration into yeast, genes are under the control of the 500 nt up-stream promotor regions form the *S. cerevisiae* glycolytic genes PGK1, TDH3 and TPI1 (blue-framed squares), the DNA segments coding for the genes ends with a termination of transcription region (purple square). Digestion of the DNA with AarI liberates flanking 50 nt nucleotide extensions that are complementary with the start and end of the gene GRE3 (green lines), whereby using commonly used method for DNA transformation of the DNA into yeast and subsequent genomic integration have replaced one of the GRE3 genes in the yeast genome or transformation may induce separate recombination of Xyl1 with native Gre3 and Xyl2 with native Sor1 or Sor2, due to high DNA sequence homology with respective closest yeast homolog Gre3 and Sor1/2. The DNA sequence also contains a number of unique restriction enzyme sites: AarI (2 sites), AscI, AsiSI, ClaI, EcoRV, MluI, MreI, NotI, NruI, PmeI, RsrII, SbfI, SgfI, SrfI, SwaI, XbaI.

In an embodiment of the invention, there is provided a method of preparing a strain of sugar fermenting *Saccha-*

*romyces cerevisiae* with capability to ferment xylose, wherein said method comprises different important procedural steps. *Saccharomyces cerevisiae* strains ferment glucose naturally and have by means of the present invention been prepared to ferment xylose as well at a high rate. Other sugars are also fermented with a strain according to the present invention, e.g. glucose, and galactose.

The present invention relates, in one aspect, to a method of preparing a strain of sugar fermenting *Saccharomyces cerevisiae* with capability to ferment xylose, wherein said method comprises the steps:

a) sporulating a first strain of *Saccharomyces cerevisiae* for providing at least 20 tetrads of said strain, b) introducing DNA, encoding for xylose reductase and xylitol dehydrogenase obtained from *Scheffersomyces stipitis* and xylulokinase obtained from *Saccharomyces cerevisiae*, into a second strain of *Saccharomyces cerevisiae*, c) mating the first sporulated *Saccharomyces cerevisiae* strain with the second *Saccharomyces cerevisiae* strain evolved on xylose and in a haploid state by mixing cells of said *Saccharomyces cerevisiae* haploid strain with each tetrad obtained in step a) to provide mated cells on an YPD agar plate, d) screening for mated cells on xylose and geneticin agar plates, e) growing mated cells from step d) in minimal defined xylose liquid medium, f) verifying that the mated cells exhibit basic morphology features of budding yeast by microscopic inspection and selecting such mated cells with basic morphological features, g) creation of a mixture of the mated cells with basic morphology features in equal amounts from step f), h) subjecting the mixture to continuous chemostat cultivation firstly in a microaerobic environment and thereafter in a anaerobic environment using feeding strategy with defined xylose medium feed for at least $0.08\ h^{-1}$ in cyclus of feed and disrupted feed in a cyclus time range of a few hours, and thereafter with constant feed for at least $0.13\ h^{-1}$, i) subjecting the mixture to continuous chemostat cultivation in an anaerobic environment with cells from step h) using lignocellulose feeding with xylose medium for at least $0.08\ h^{-1}$ in cyclus of feed and disrupted feed in a cyclus time range of a few hours, and with constant feed rate for at least $0.13\ h^{-1}$, j) obtaining the sugar fermenting *Saccharomyces cerevisiae* cells with capability to ferment xylose by collecting said cells from the chemostat reactor, k) diluting the cells from chemostat into water, then plating cells onto YPD agar plate to obtain single colonies, and incubating at 30° C. for at least 4 days, l) determining the DNA sequences of any retained and/or evolved enzymes for maximum xylose fermentation, The yeast as obtained by the present inventive method as described above comprises a new gene Gre3 (YHR104w), referred to as the modGre3 gene, which is present with >60% identical in pair-wise amino acid sequence alignment with native Gre3. Thus, the yeast obtained is not encoding Xyl1 (encoding xylose reductase) and Xyl2 (encoding xylitol dehydrogenase) from *Scheffersomyces stipitis*. The new gene modGre3 gene as defined herein is a new gene encoding for the amino acid sequence (Seq Id No 1) as defined in FIG. 24 and in the sequence listing. The strains of the invention including the modGre3 gene have >5 times higher in vitro xyloses reductase activity compared with *Saccharomyces cerevisiae* strain USM21 (CBS102678) containing the native Gre3 gene.

The upregulated enzymatic activities for xylose conversion in the strains of the invention are xylose reductase from modGre3 and native xylitol dehydrogenase enzymes Xdh1 and Sor1/2 as well as of xylulokinase XKS1 for formation of xylulose-5-phosphate formation. At least one copy of xylulokinase XKS1 is under the control of a strong glycolytic promotor, such as the +500 nt region of the triose phosphate isomerase promotor. In addition, the absence of recombinant xylose reductase and xylitol dehydrogenase from *Scheffersomyces stipitis* has been verified. Thus, isolating strains according to the invention with an increase in enzymatic activities of a factor >5 of xylose reductase and xylitol dehydrogenase in enzymatic coupled assay monitoring absorbace change at 340 nm with NADH/NADPH or NAD+ as co-substrate has been performed.

Thus, according to the invention, a strain of *Saccharomyces cerevisiae* comprising at least one native XKS1 gene in its genome encoding xylulokinase, at least one native XDH1 gene in its genome encoding xylitol dehydrogenase, and at least one modGre3 gene in its genome, said modGre3 gene encoding an amino acid sequence of SEQ ID NO 1 having xylose reductase activity or encoding a fragment of said amino acid sequence having xylose reductase activity, has been provided.

The method of obtaining the inventive strains of the present invention comprises the following steps.

Step a) concerns sporulating a first strain of *Saccharomyces cerevisiae* for providing at least 20 tetrads of said strain, wherein this step proceeds for at least 1 week at at least room temperature. A temperature in the range of 20-30° C. provides the desired results. Sporulating *Saccharomyces cerevisiae* is performed as in its ordinary sense within the technical field.

Step b) concerns introducing DNA, encoding for xylose reductase and xylitol dehydrogenase obtained from *Scheffersomyces stipitis* that have high DNA sequence homology with respective closest yeast homologue Gre3 and Sor1/2 and xylulokinase obtained from *Saccharomyces cerevisiae*, into a second strain of *Saccharomyces cerevisiae*.

Step c) concerns mating the first sporulated *Saccharomyces cerevisiae* strain with the second *Saccharomyces cerevisiae* strain evolved on xylose and in a haploid state by mixing cells of said *Saccharomyces cerevisiae* haploid strain with each tetrad obtained in step a) to provide mated cells on an YPD agar plate, wherein this step proceeds for at least 1 week at at least room temperature. A temperature in the range of 20-30° C. provides the desired mating results.

Step d) concerns screening for mated cells on xylose and geneticin agar plates, wherein the xylose and geneticin agar plates comprises 50-150 µg/ml geneticin, preferably about 100 µg/ml geneticin, and 15-25 g/L xylose, preferably 20 g/L xylose. In an embodiment of the invention, the first strain of *Saccharomyces cerevisiae* is USM21 (CBS102678) and the second strain of *Saccharomyces cerevisiae* originates from Taurus 1 (CBS102679) with extra copies of XYL1, XYL2 and XKS1, that has the β-lactamase genes removed and has been evolved for efficient xylose fermentation and is in an haploid state.

The evolved xylose fermenting haploid strain, can grow on xylose, but it is not resistant to the geneticin antibiotic, while USM21 can not grow on xylose but is resistant to geneticin. Therefore, it is only the mated cells that are able to grow on the geneticin+xylose plate. The resistance of USM21 is not from a transformation of the geneticin resistance gene. The resistance of USM21 to grow on the geneticin is gained by some cellular mechanism.

Step e) concerns growing mated cells from step d) in minimal defined xylose liquid medium, wherein the minimal defined xylose liquid medium is for example in the range 15-25 g/L xylose, preferably about 20 g/L xylose, defined medium liquid culture. This step is performed in order to quantitatively increase the amount of cells.

Step f) concerns verifying that the mated cells exhibit basic morphology features of budding yeast by microscopic inspection and selecting such mated cells with basic morphological features. To a person skilled in the art it is clear which type of mated cells, exhibiting basic morphological features of budding yeast, are and can be chosen from the microscopic inspection.

Step g) concerns creation of a mixture of the mated cells with basic morphology in equal amounts from step f), wherein the equal amounts of the basic, mated cells in this step is typically in the range of $1 \times 10^6$ cells/ml-$1 \times 10^8$ cells/ml, especially about $0.5 \times 10^7$-$2 \times 10^7$ cells/ml.

Step h) concerns subjecting the mixture to continuous chemostat cultivation firstly in a microaerobic environment and thereafter in a anaerobic environment using feeding strategy with defined xylose medium feed for at least 0.08 $h^{-1}$ in cyclus of feed and disrupted feed in a cyclus time range of a few hours, and thereafter with constant feed for at least 0.13 $h^{-1}$. The dilution rate ($h^{-1}$) can be adjusted in order to obtain cells with correct characteristics.

Step i) concerns subjecting the mixture to continuous chemostat cultivation in an anaerobic environment with cells from step h) using lignocellulose feeding with xylose medium for at least 0.08 $h^{-1}$ in cyclus of feed and disrupted feed in a cyclus time range of a few hours, and with constant feed rate for at least 0.13 $h^{-1}$.

Step j) concerns obtaining the sugar fermenting *Saccharomyces cerevisiae* cells with capability to ferment xylose by collecting said cells from the chemostat reactor, and step k) concerns diluting the cells from chemostat into water, then plating cells onto YPD agar plate to obtain single colonies, and incubating at 30° C. for 4 days.

It is well-known that wild-type yeast cannot ferment xylose into ethanol, especially high rates of anaerobic conversion of both glucose and (<0.5 g/h/CWD) xylose into ethanol has not been documented for any other fungus including Saccharomycetales non-yeast species. All non-yeasts that ferment xylose require at least micro aerobic conditions, but then also forms substantial amounts of, even mainly, xylitol from the xylose. In the method of the invention a combination of techniques has been provided, like sporulation of diploid strains to form tetrads, evolutionary engineering and homologous recombination between different strains. Traits (eg phenotypical characteristics) essential for inhibitory tolerance have been mated with xylose fermenting traits using a new technique where only the diploid mated strain is able to grow. It has never been reported before the present invention that it is possible to select for the diploid mated strain directly after mixing of two haploid strains on an agar plate, i.e. step d) as described above. The diploid strain is then in the following steps adapted for efficient xylose fermentation in a carefully monitored procedure where the key observables are lowest possible xylitol and glycerol formation, while maximizing xylose uptake. In the final >40 generation is the strain adaptation performed in presence of ligno-cellulose and glucose and xylose. No other prior art publications have evolutionary engineered a slowly fermenting xylose strain crossed with a wild-type wine strain (i.e. USM21, CBS 102678), where only the mated cells are in the starting cell population. Genetic traits from the wild-type non-xylose fermenting strain has been determined to be present in the crossed xylose fermenting strains, thereby verifying genetically that cell mating has indeed occurred. Also, the evolutionary engineering is done in a new carefully monitored method where the key parameters were both to minimize xylitol and glycerol by-product formation while maintaining or increasing biomass yields and/or ethanol formation. There was a step-wise increase in selection of a higher xylose uptake rate, in first aerobic xylose defined media, then in anaerobic defined media followed by feeding lignocellulose media with both glucose and xylose present.

The present invention relates also to a strain of *Saccharomyces cerevisiae* obtainable by the method as described above.

The cells ferment xylose efficiently in addition to sugars as it ferments normally, i.e. glucose and sucrose etc.

In an embodiment of the invention the second *Saccharomyces cerevisiae* haploid strain is obtained from the deposited yeast strains Taurus01 with deposit number CBS 102679, deposited May 1, 2000, Taurus03 with deposit number CBS128138, deposited on Oct. 26, 2010, Taurus04 with deposit number CBS 128139, deposited on Oct. 26, 2010, Taurus07 with deposit number CBS128140, deposited on Oct. 26, 2010, Taurus10 with deposit number CBS128141, deposited on 2 Nov. 2010, at Centraalbureau voor Schimmelcultures, Uppsalalaan 8, 3584 CT Utrecht, the Netherlands. The above strains as used in the method according to the invention have the β-lactamase gene(s) removed, and are evolutionary engineered for increased xylose uptake rates using chemostat cultivation and repetitive batch with both defined xylose medium and lignocellulose.

In an embodiment of the invention, the first strain of *Saccharomyces cerevisiae* for providing at least 20 tetrads of said strain is *Saccharomyces cerevisiae* USM21 with deposition number CBS102678, deposited at Centraalbureau voor Schimmelcultures (CBS), Delft, the Netherlands. In another embodiment of the invention, a strain of *Saccharomyces cerevisiae* is obtainable by the method as described above.

In creation of robust xylose fermenting yeast strains it is needed to perform multiple steps in order to adjust the yeast metabolism to accommodate efficient and fast anaerobic xylose fermentation. The previous and prior art attempts to induce higher rates of xylose fermentation using a stated mating procedure have failed to prove that actual mating has occurred, see eg WO2005121337 and WO2009155633, and the xylose is consumed when the yeast is propagated in aerobic environment. In the anaerobic fermentation of ligno cellulose only glucose and galactose is fermented into ethanol, and only <20% of the xylose is converted, but then to xylitol, as disclosed in WO2009/155633. In the anaerobic fermentation of lignocellulose only glucose and galactose is fermented into ethanol, and only <20% of the xylose is converted, mainly towards xylitol, as disclosed in eg WO2005121337 and WO2009155633. In the anaerobic fermentation of lignocellulose glucose, galactose and xylose is fermented into low total amounts <18 g/L of ethanol, but ~20% of the xylose is converted into xylitol, as disclosed in WO2006/115455.

As stated above, a strain of *Saccharomyces cerevisiae* comprising at least one XKS1 gene in its genome encoding xylulokinase, at least one native XDH1 gene in its genome encoding xylitol dehydrogenase, and at least one modGre3 gene in its genome, said modGre3 gene encoding an amino acid sequence of SEQ ID NO 1 having xylose reductase activity or encoding a fragment of said amino acid sequence having xylose reductase activity has been obtained according to the method as described herein. The above mentioned genes are present in the strain of *Saccharomyces cerevisiae* in addition to the native genes as present in *Saccharomyces cerevisiae*. Very efficient strains have been provided in accordance with the invention both regarding ethanol production and small by-product formation such as xylitol.

In one embodiment of the invention, the above mentioned specific genes of XKS1 and/or XDH1 and/or modGre3 are present in *Saccharomyces cerevisiae* in one copy or more of said genes, eg one, two or more copies. In addition, the before mentioned genes may be present together with other natural genes present also encoding xylulokinase activity, xylitol dehydrogenase activity, and xylose reductase activity. It is understood that variants of the XKS1 gene and XDH1 gene are also covered by the invention as long as the enzyme activities xylulokinase activity, and xylitol dehydrogenase activity are encoded.

In one embodiment of the invention, the fragment of said amino acid sequence has at least 85% identity or at least 90% identity, e.g 91%, 92%, 93%, 94% or 95% identity or 96%, 97%, 98% or 99% with the sequence of SEQ ID NO 1 and having xylose reductase activity. As long as the fragment of the SEQ ID NO 1 has the xylose reductase activity it is covered by the present invention. To a skilled person it is realized which amino acids could be exchanged without affecting the xylose reductase activity of the amino acid sequence encoded from the modGre3 gene. A skilled person knows which amino acids are similar and could be exchanged with one another without affecting the xylose reductase activity.

Additionally, in determining amino acid similarity between the fragment of SEQ ID NO 1 and SEQ ID NO 1, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Possible conservative amino acids substitution groups are: valine-leucine-isoleucine, phenylalanine-tyrosine, lysine-arginine, alanine-valine, and asparagine-histidine-glutamine. Substitutional variants of the amino acid sequence disclosed herein are those in which at least one residue in the disclosed sequences has been removed and a different residue inserted in its place. Possible conservative substitutions for each of the naturally occurring amino acids are as follows: Ala to ser; Arg to lys; Asn to Gln or his; Asp to glu; Cys to ser or ala; Gln to asn; Glu to asp; Gly to pro; His to asn or gin; Ile to leu or val; Leu to ile or val; Lys to arg; Gln or glu; Met to leu or ile; Phe to met, leu or tyr; Ser to thr; Thr to ser; Trp to tyr; Tyr to trp or phe; and, Val to ile or leu.

The present invention also covers the nucleic acid sequence encoding an amino acid sequence as described in the sequence listing or a fragment thereof as described above having xylose reductase activity.

A fragment, as discussed herein, is a polypeptide having an amino acid sequence that is entirely the same as part but not all of the amino acid sequence of SEQ ID NO 1. A fragment may be "free-standing" or comprised within a larger polypeptide of which they form a part or region. Thus, a fragment may be shorter than the full-length sequence of SEQ ID NO 1 or if comprised within a larger peptide may be longer.

In an embodiment of the invention, an exemplary strain and obtained according to the method as described above is *Saccharomyces cerevisiae* Taurus 13 having deposition number CBS137333 deposited on Feb. 18, 2014, at Centraalbureau voor Schimmelcultures, Uppsalalaan 8, 3584 CT Utrecht, the Netherlands. Other exemplary strains are *Saccharomyces cerevisiae* Taurus 14 having deposition number CBS 137663, *Saccharomyces cerevisiae* Taurus 15 having deposition number CBS 137664, *Saccharomyces cerevisiae* Taurus 16 having deposition number CBS 137665, or *Saccharomyces cerevisiae* Taurus 17 having deposition number CBS 137666, which all have been deposited on Apr. 15, 2014, at Centraalbureau voor Schimmelcultures, Uppsalalaan 8, 3584 CT Utrecht, the Netherlands. All of the *Saccharomyces cerevisiae* strains as mentioned above comprise the amino acid sequence as disclosed in SEQ ID NO 1.

In another embodiment, the present invention relates to the use of a strain of *Saccharomyces cerevisiae*, as exemplified above and prepared according to above described method, for fermentation of sugar containing hydrolysates to ethanol, wherein said sugar is chosen from the group sucrose, glucose, xylose, fructose, mannose, arabinose and galactose or any combination thereof. The hydrolysate may contain one or more of above mentioned sugars and other sugars not specifically mentioned here. The pH of said sugar containing hydrolysates is preferably in the range of 4-6, but fermentation of a hydrolysate could also function at pH below or above the range 4-6. In an embodiment of the invention the sugar containing hydrolysate is a lignocellulose hydrolysate. Hydrolysates are typically liquid. The strains of the invention are very robust and auxotrophic and can ferment ligno-cellulose streams without nutrient supplementation. Many fermentation results using the strains of the invention are obtained in absence of any nutrient supplementation. The composition of the hydrolysates determines whether nutrients need to be added or not. However, as have been shown in the experimental part, it is not necessary at all instances, which is beneficial from an economic point of view. Common and non-limiting nutrient supplementations are 0.2-1 g/L of urea, magnesium sulphate, and corn steep liquor. Nutrients may be added to the fermentations but it is not always necessary according to the invention. By excluding the nutrient supplementation the process of the invention will be cost efficient. The strain according to the invention can also ferment hydrolysed solid materials such as pretreated biomass or any other sugar containing solid material, e.g. wheat starch and corn mash.

There are many different sugar containing hydrolysates and lignocellulose hydrolysates available within the technical field and any such hydrolysates may be used together with the *Saccharomyces cerevisiae* strain as prepared according to the method of the present invention. The lignocellulose hydrolysates may be chosen from any agricultural or forest residues such as energy crops and whole crop. Examples of such lignocellulose hydrolysates are energy grass hydrolysates, bagasse hydrolysates, straw hydrolysates, e.g. wheat straw hydrolysates, corn cob hydrolysates, sugar cane hydrolysates, hardwood hydrolysates, softwood hydrolysates, e.g. birch hydrolysates, corn stover hydrolysates and any combination thereof. The above list is non-exhaustive. By the findings of the present invention xylose, for instance present in a lignocellulosic hydrolysate, is reduced to xylitol and further oxidized to D-xylulose and metabolized to pyruvate. The desired end product as disclosed herein is ethanol, but could also be another end product such as an acid, 3-hydroxy-propionic acid, acrylic acid, succinic acid, and citric acid or any other platform chemical as long as the host strain contains other metabolic traits for such conversion.

The amount of ethanol produced by a strain of the invention is in the range 35-51 g ethanol/100 g consumed xylose and glucose, eg 35, 40, 45 or 50 g or any specific value in between 35-51 ethanol/100 g consumed xylose and glucose, 1-2 g xylitol/100 g consumed xylose and 1-8 g glycerol/100 g consumed xylose and glucose, eg 2, 3, 4, 5, 6, 7 g glycerol/100 g consumed xylose and glucose.

The fermentation of sugar containing hydrolysates with a strain according to the invention can take place in a batch fermentation, a fed-batch fermentation, a continuous fermentation, in a simultaneous saccharification and fermentation (SSF) process, in a simultaneous saccharification and co-fermentation (SSCF) process or a prehydrolysis and simultaneous saccharification and fermentation (PSSF) process.

In an embodiment of the invention the use of a strain, as prepared, when fermenting a sugar containing hydrolysate leads to high ethanol yields. The strains co-consume glucose and xylose when [Glc]<60 g/L and glucose is consumed at a 3-10 times higher rate than xylose, also the xylose consumption rate is dependent of the residual glucose concentration. And hence, if [Glc] is 3 to 80 g/L (x) and [Xyl] is 5 to 37 g/L (y) is the equation y=−0.12+7.2 attained for the strains of the present invention (FIG. 7, 14-17). That is, at residual glucose concentration of 40 g/L is (−0.12*40 g/L+ 7.2)=2.4 g/L xylose consumed at the same time as 24 g/L glucose is consumed. While at [Glc]=17 g/L, is (−0.12*17+ 7.2)=5.2 g/L xylose consumed at the same time as 16 g/L glucose.

It has been shown that the strains of the invention can handle both high and low concentrations of both xylose and glucose.

The amount of sugar, preferably xylose and glucose, in the medium for anaerobic fermentation by a strain of the invention is >100 g/L, for example >200 g/L or any value there between. A range of 150-250 g/L sugar, eg 160, 170, 180, 190, 200, 210, 220, 230, 240 g/L sugar or any specific value in said interval, is possible to ferment by using a strain of to the invention. In an embodiment of the invention, the concentration of xylose is >10 g/L xylose and/or the concentration of glucose is >10 g/L. The sugars fermented could be glucose, xylose, galactose and arabinose, which are present in lignocelluloses hydrolysates.

In another embodiment of the invention, the use of a strain as prepared, when fermenting a sugar containing hydrolysate leads to high ethanol yields even in the presence of inhibitors such as from furfural, HMF, formic acid, leuvulinic acid, acetic acid and phenolics.

Thus, according to the present invention, robust *Saccharomyces cerevisiae* strains have been obtained providing high ethanol yields, low by-product yields such as xylitol even in the presence of high concentrations of inhibitors. Thus, a strain that ferments xylose, in addition to other sugars present, in lignocellulose material at a yield of 35-51 gram ethanol per 100 gram consumed xylose and glucose has been provided. The strain according to the present invention has a high xylose consumption rate that is close to that of glucose consumption rate, which is highly desirable. The strain according to the present invention can propagate in a defined xylose medium at a specific growth rate of mu=0.25 h$^{-1}$ (+−0.02).

The strain of the invention is free from the β-lactamase gene, an antibiotic resistance gene often introduced upon genetic engineering of the yeast for obtaining new traits.

It has been shown clearly that a strain according to the present invention can perform well in anaerobic fermentation of xylose in five different types of hydrolysates (bagasse, birch, wheat straw, corn stover and hard wood).

The strain of the invention converts only 1-2% of the consumed xylose into xylitol, see FIGS. 4-23.

In addition, a strain according to the present invention is able to ferment >98.5% of available xylose.

All technical terms used in the present application have the meaning as is commonly understood by the skilled man.

The strains of the invention may be prepared from industrial yeast strains as well as laboratory yeast strains even though industrial yeast strains are preferred. An industrial strain is less well defined than the laboratory strains since it has several copies of each chromosome. Thus, manipulating industrial strains, as have been performed according to the present invention, is a larger challenge.

EXPERIMENTAL DESCRIPTION

Experiment 1

Method description for constructing a strain according to present invention. Strain sporulation of USM21 (CBS102678) and mating with evolved haploid xylose fermenting strain originating from CBS102679 and CBS128139. Day 1: Yeast strain USM21 (CBS102678) was streaked onto an YPD agar plate and incubated at 30° C. for 3 days. Another yeast strain with introduced DNA so as to cause the yeast (*Saccharomyces cerevisiae*) to obtain a second set of the genes encoding xylose reductase and xylitol dehydrogenase obtained from *Scheffersomyces stipitis* and xylulokinase obtained from *S. cerevisiae* and evolved for xylose fermentation is haploid (hereafter referred to as strain evolved) was streaked on to 20 g/L xylose agar plate and plates incubated at 30° C. for 4 days.

Day 5: USM21 cells was transferred onto a 2% KAc agar plate, and left at 30° C. 4 days, and room-temperature for 3 days. The strain had by then sporulated and individual spores were digested from each other by treatment with 1 mg/ml Lyticase in 10 mM Tris pH 7.5 with 1 mM EDTA for 40 min at 30° C. Individual spores were moved using a dissecting instrument onto a YPD plate and mixed with 1 to several cells of strain evolved. More than 20 such mixes were made. 4 spores from USM21 were also placed on the YPD plate without cells from evolved xylose strain. Plate was incubated at 30° C. for 5 days.

Day 10: Colonies appeared where the mixture USM21 and evolved xylose strain had been placed, these potentially containing newly mated cells. There were also colonies on the places where only dissected USM21 spores had been placed. Both these types of colonies where picked as well as separate colonies from a xylose agar plate with the evolved strain and grown over-night in liquid YPD medium then getting $OD_{600}$=2-5. Equal amounts of cells with mated USM21+evolved strain cultures were mixed and the OD set to 0.1, 0.01 and 0.001 by dilution into water. Then 50 µl of the different OD mixtures were placed onto a xylose-geneticin plate. On the same plate corresponding drops of the single original strains (USM21 and evolved strain) were also placed. The plate was incubated at 30° C. for 5 days.

Day 15: Colonies only appeared in the drop where the OD=0.1 with the mated USM21 and evolved xylose strain cell drop was placed. There was no growth of the cells with only newly dissected USM21 cells or evolved strain added. A few dozen individual colonies where picked of the strain crosses using the dissecting instrument onto a YPD plate with 20 g/L glucose. The YPD plates with the crossed strains were then incubated for 4 days at 30° C.

Day 19: A few dozen colonies were then inspected in the microscope, and only those cells were used that were from colonies that contained cell types that looked like typical budding yeast (like a small and a large egg together). 20 different colonies were grown in individual vials over-night with 15 ml 20 g/L glucose minimal medium in each. A mixture of cells was created adding an equal amount of cells to make the final OD=2.0 in 10 ml, corresponding to $1\times10^8$ cells. This mixture was then grown aerobically on xylose for 2 weeks in a volume of 100 ml in a shake flask at 130 rpm at 30° C., followed by 2 weeks of semi aerobic growth in a chemostat cultivation in a stirred shake flask at 300 rpm, with defined medium 15 g/L xylose feed into the reactor, at a dilution of mu=0.05 $h^{-1}$ with pH4.5-5.5 at 25-30° C.

Figures 2A, 2B:
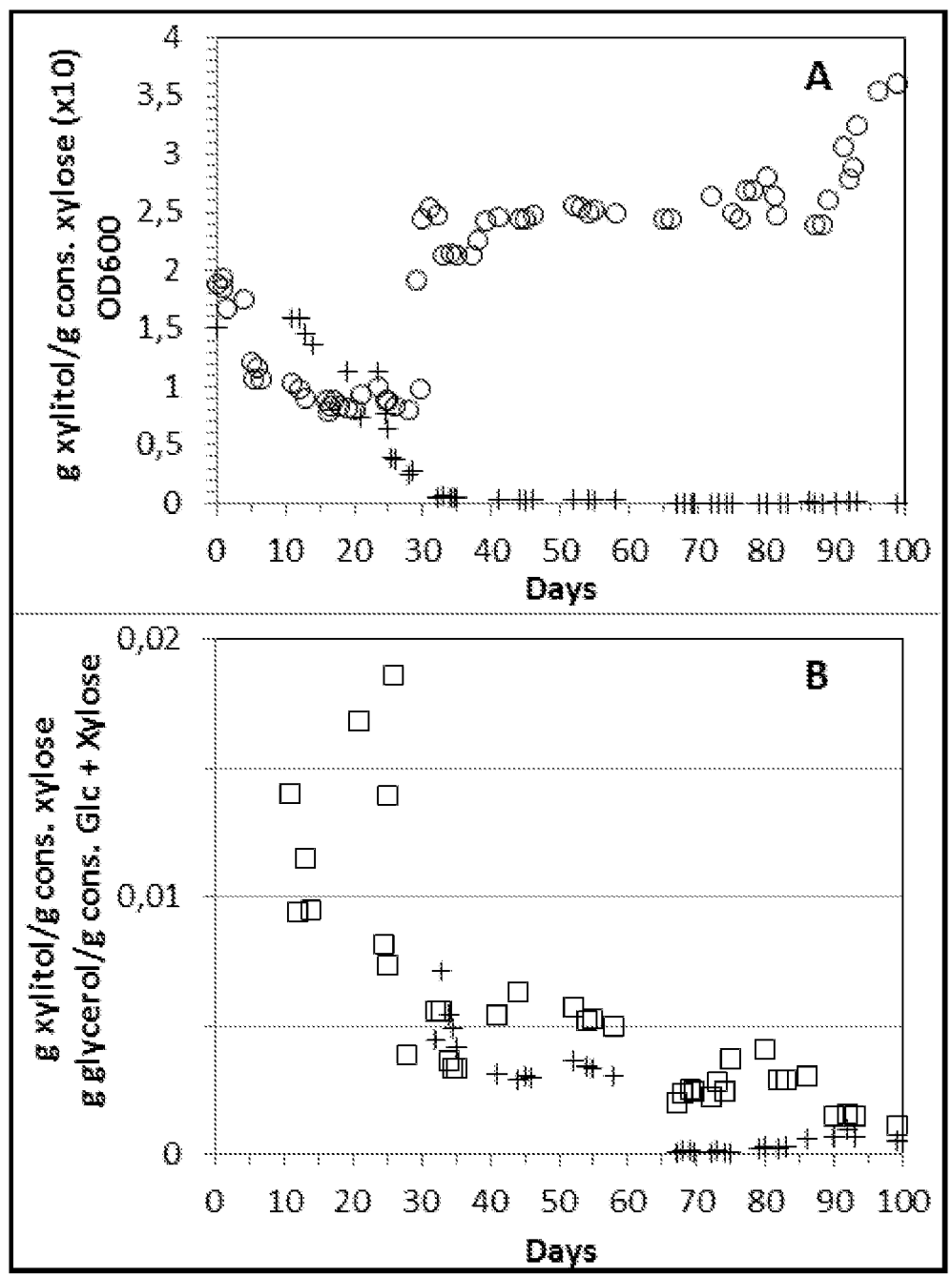
FIG. 2. Evolutionary engineering of yeast for efficient anaerobic xylose fermentation in a chemostat. A defined medium with 15 g/L xylose medium is used Day0 to Day64, and a ligno cellulose feed with 30 g/L xylose+0.6 g/L glucose is used from Day65 to Day99. A: OD$_{600}$ (open circles) and g xylitol/g consumed xylose (cross); B: g xylitol/g consumed xylose (cross) is re-scaled along y-axis from FIG. 2A, and in 2B is also shown g glycerol/g consumed glucose+xylose. Within the first time-period, a decreased xylitol production is obtained (0-30 Days), where after, during Day30 to Day40, a metabolic adjustment has occurred and yeast is able to metabolise the xylose more efficiently to produce more biomass seen as higher optical density at 600 nm (OD$_{600}$) at days 30-35. Further, there is a decrease in glycerol production occurring during the whole chemostat cultivation so that <0.3% of the sugars is converted into the by-products xylitol and glycerol.
Figure 3:
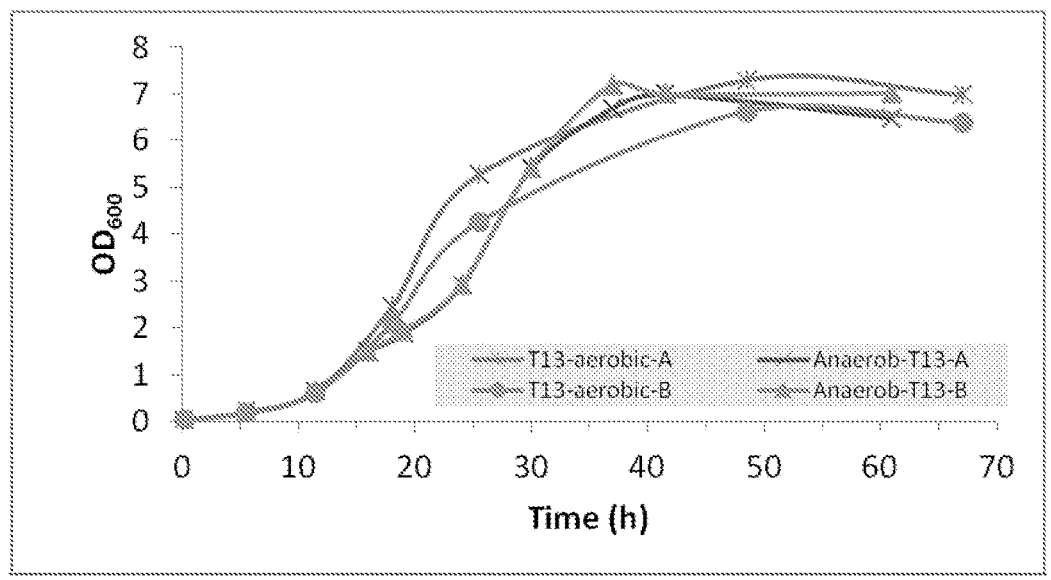
FIG. 3. Cell propagation behaviour of the strain of the invention using Taurus13 in defined medium during aerobic and anaerobic condition in defined medium using 100 g/L glucose and 75 g/L xylose. Glucose is consumed within 24 h and xylose before 50 h. Aerobic and anaerobic propagations are started at optical density of 0.1 and 1.5, respectively.
Figure 4:
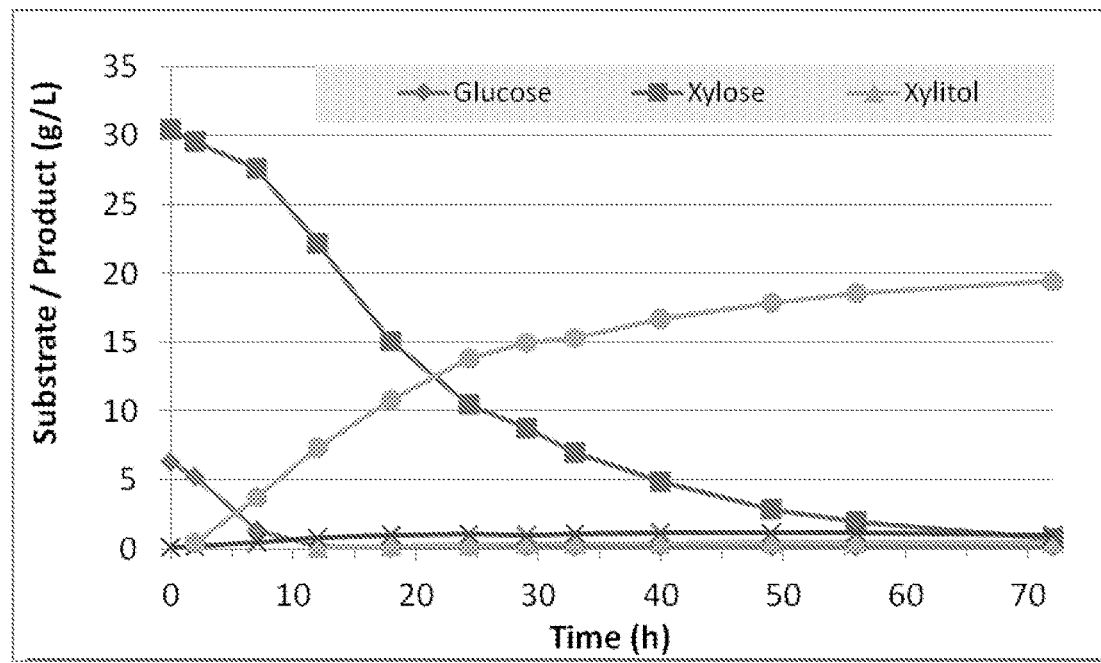
FIG. 4. Anaerobic fermentation of glucose and xylose with a strain of the invention using Taurus13 in wheat straw hydrolysate at pH5. Glucose fermentation phase starts at ~3 h when the inhibitors HMF (0.1 g/L), furfural (2.0 g/L) have been metabolised, the medium also contains 2.6 g/L acetate. Glucose is fermented within 8 h, and xylose is completely fermented at 60 h. There is only 1.2 g/L glycerol and 0.6 g/L xylitol at the end of the fermentation, corresponding to very low by-product formation, <3% of the fermented sugar.
Figure 5:
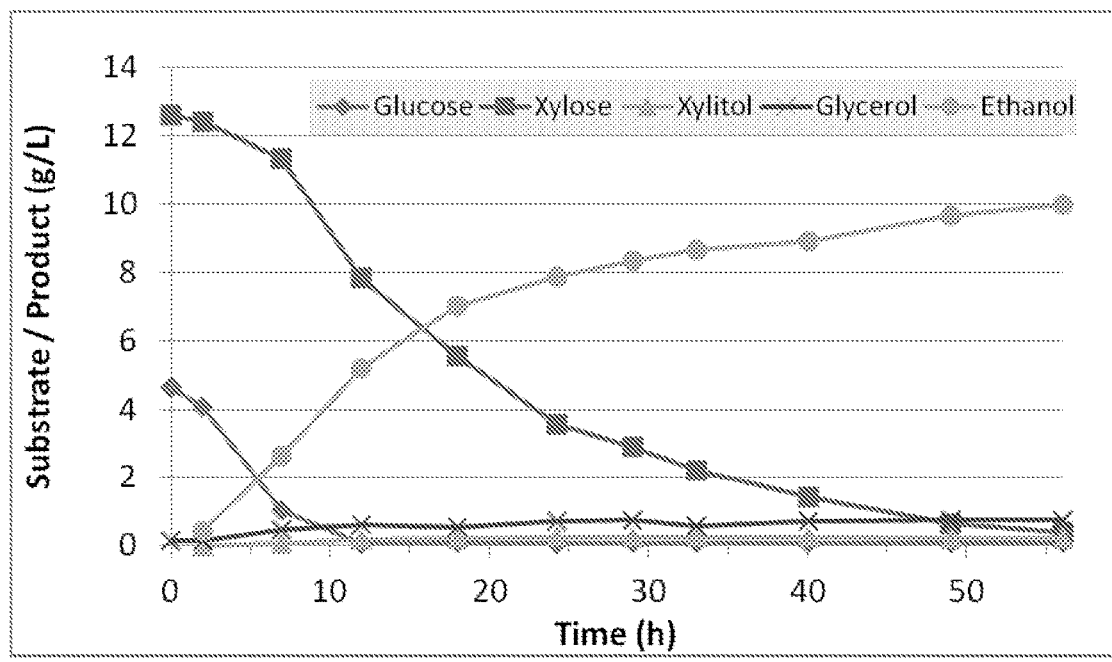
FIG. 5. Anaerobic fermentation of glucose and xylose with a strain of the invention using Taurus13 in bagasse hydrolysate at pH5. Glucose fermentation phase starts at 3 h when the inhibitors HMF (0.1 g/L), furfural (1.8 g/L) have been metabolised, the medium also contains 9.5 g/L acetate. Glucose is fermented within 10 h, and xylose is completely fermented at 50 h. There is only 0.7 g/L glycerol and 0.25 g/L xylitol at the end of the fermentation, corresponding to a by-product formation of 4% glycerol of the fermented sugar and 2% xylitol of the fermented xylose.
Figure 6:
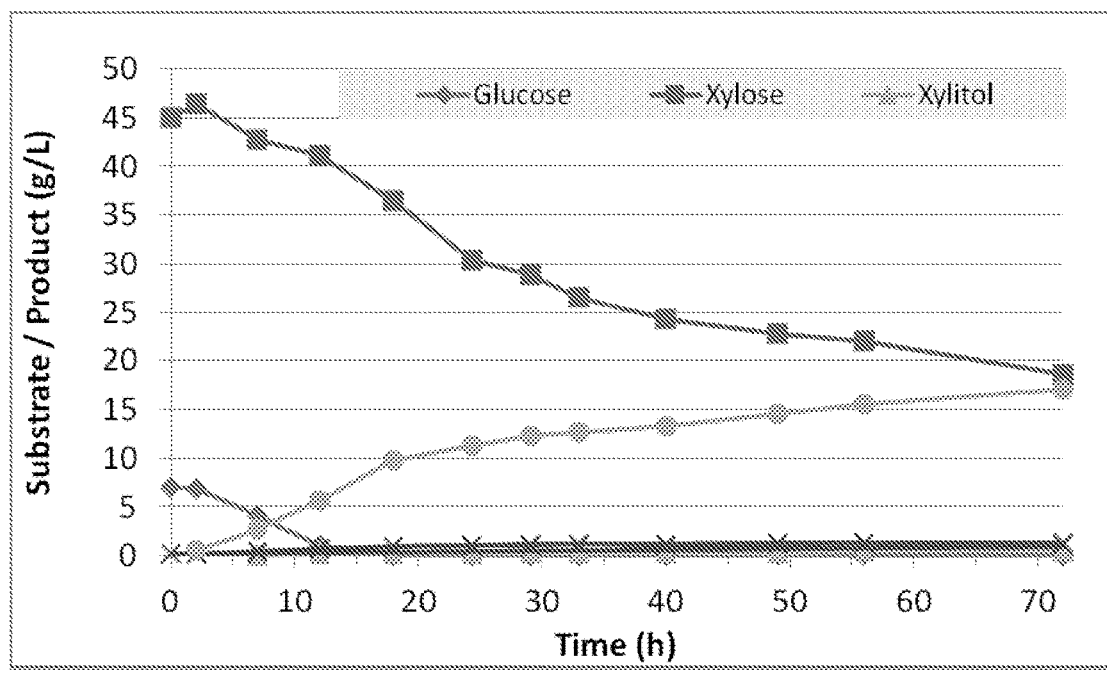
FIG. 6. Anaerobic fermentation of glucose and xylose with a strain of the invention using Taurus13 in birch hydrolysate at pH 6.0. Glucose fermentation phase starts at 2 h when the inhibitors HMF (0.1 g/L) and furfural (1.6 g/L) have been metabolised, the medium also contains 9.5 g/L acetate. Glucose is fermented within 11 h, and xylose is continously fermented during the whole 60 h experiment. There is only 1.2 g/L glycerol and 0.4 g/L xylitol at the end of the fermentation, corresponding to very low by-product formation, <1% of the fermented sugar.
Figure 7:
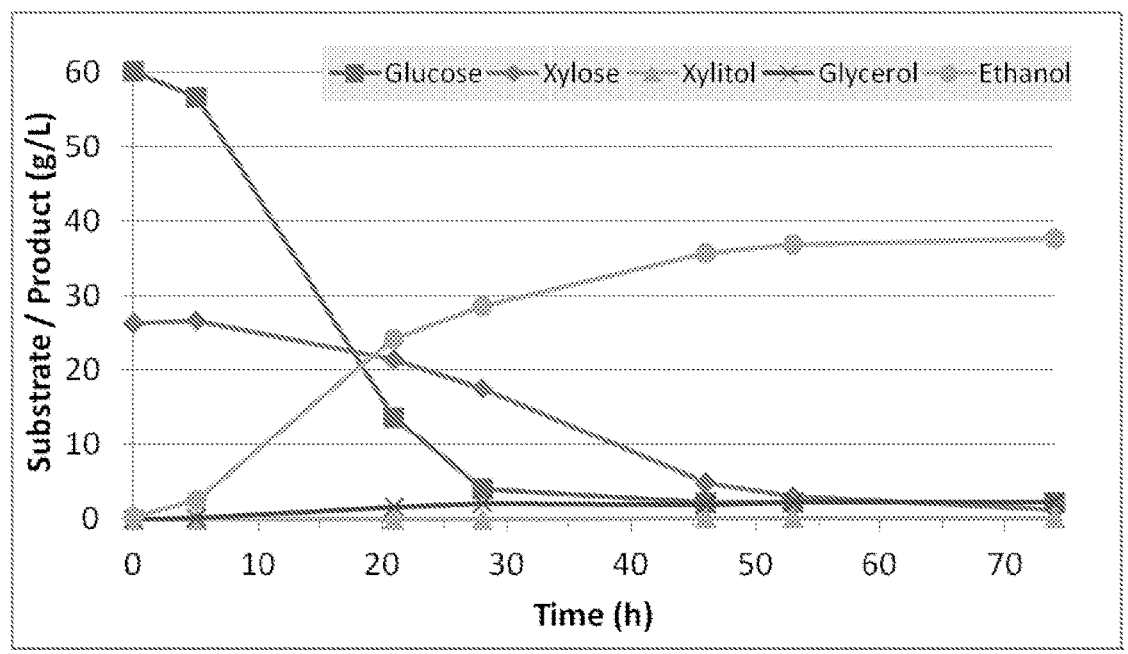
FIG. 7. Anaerobic fermentation of glucose and xylose with a strain of the invention using Taurus13 in corn stover hydrolysate at pH5. Glucose is fermented within 28 h, and xylose is completely fermented at 52 h. There is only 3 g/L glycerol and 0.2 g/L xylitol at the end of the fermentation, corresponding to very low by-product formation, <3% of the fermented sugar.
Figure 8:
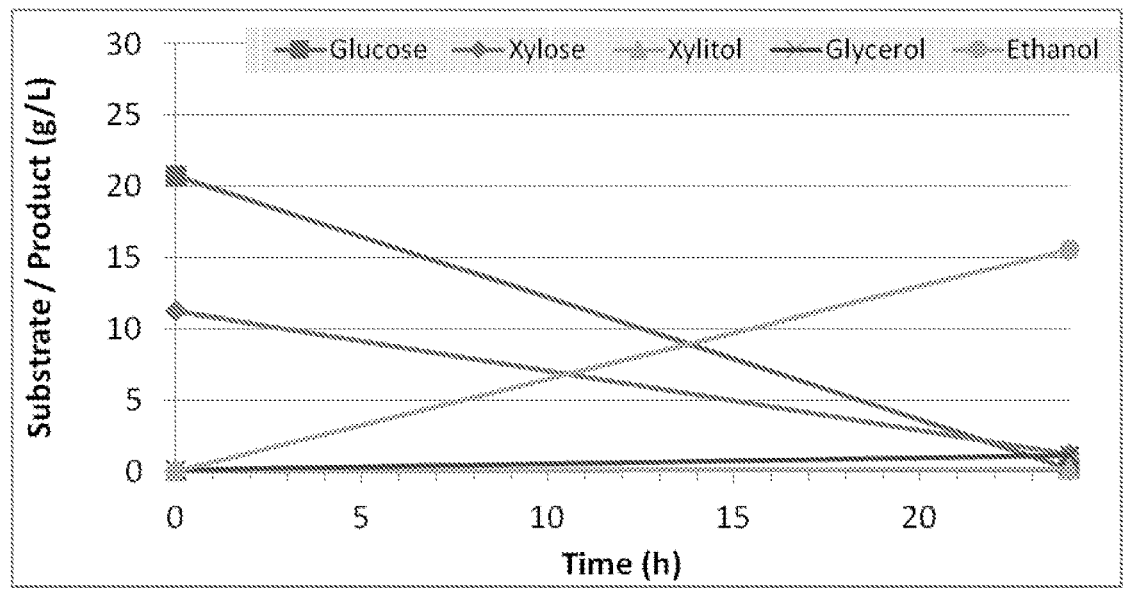
FIG. 8. Anaerobic fermentation of glucose and xylose with a strain of the invention using Taurus13 in hard wood hydrolysate at pH5.5. Glucose and xylose is fermented within 24 h. The medium also contains 2.1 g/L acetate. There is 1.2 g/L glycerol and 0.2 g/L xylitol at the end of the fermentation, by-product formation of glycerol is 4% of the fermented sugar and 2% xylitol of the fermented xylose.
Figure 9:
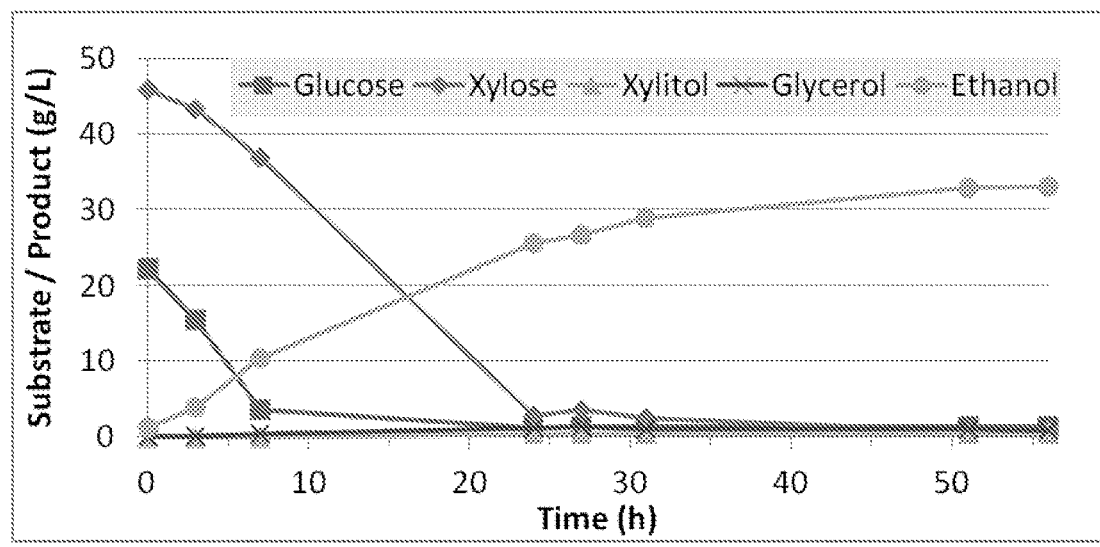
FIG. 9. Anaerobic SSF fermentation of glucose and xylose with a strain using Taurus13 of the invention in wheat straw at pH 5.0. The inhibitors HMF (0.15 g/L) and furfural (1.3 g/L) are present and have been metabolised within 3 h, the medium also contains 1.2 g/L acetate. At time 24 h 10% WIS from pre-treated wheat straw is added together with 10 FPU/g WIS of cellulose degrading enzyme mixture. At 55 h the ethanol production has occurred at high yields, and there is only a minute formation of the by-products xylitol and glycerol. The strain reaches high ethanol yields in the presence of high concentrations of inhibitors. SSF=Simultaneous Saccharification and Fermentation.
Figure 10:
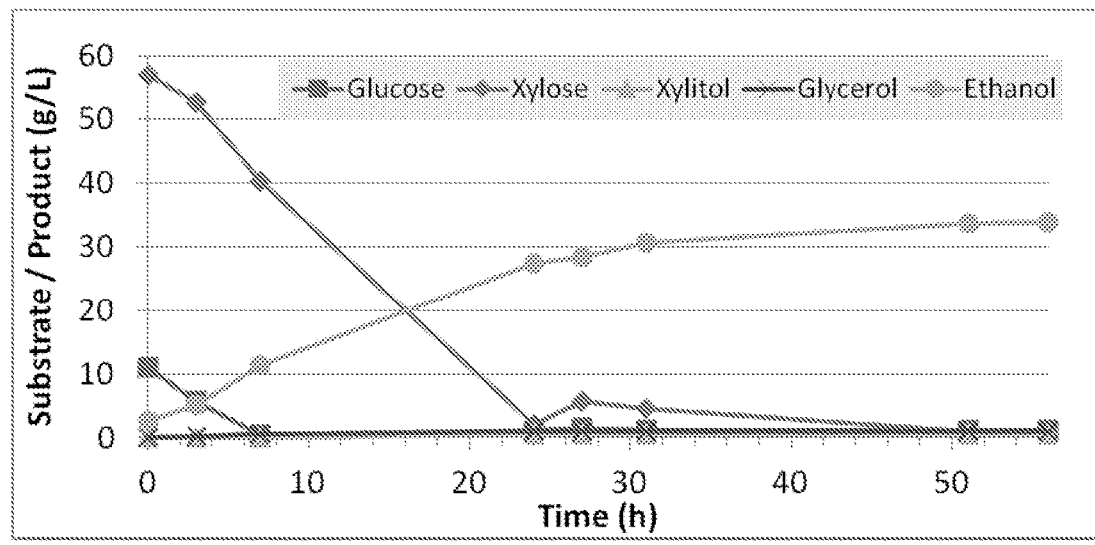
FIG. 10. Anaerobic SSF fermentation of glucose and xylose with a strain of the invention using Taurus13 in corn cobs at pH 5.0. The inhibitors HMF (0.1 g/L) and furfural (1.5 g/L) are present and have been metabolised within 3 h, the medium also contains 3.5 g/L acetate. At time 24 h 10% WIS from pre-treated wheat straw is added together with 10 FPU/g WIS of cellulose degrading enzyme mixture. At 56 h the ethanol production has occurred at high yields, and there is only a minute formation of the by-products xylitol and glycerol. The strain reaches high ethanol yields in the presence of high concentrations of inhibitors. SSF=Simultaneous Saccharification and Fermentation.
Figure 11:
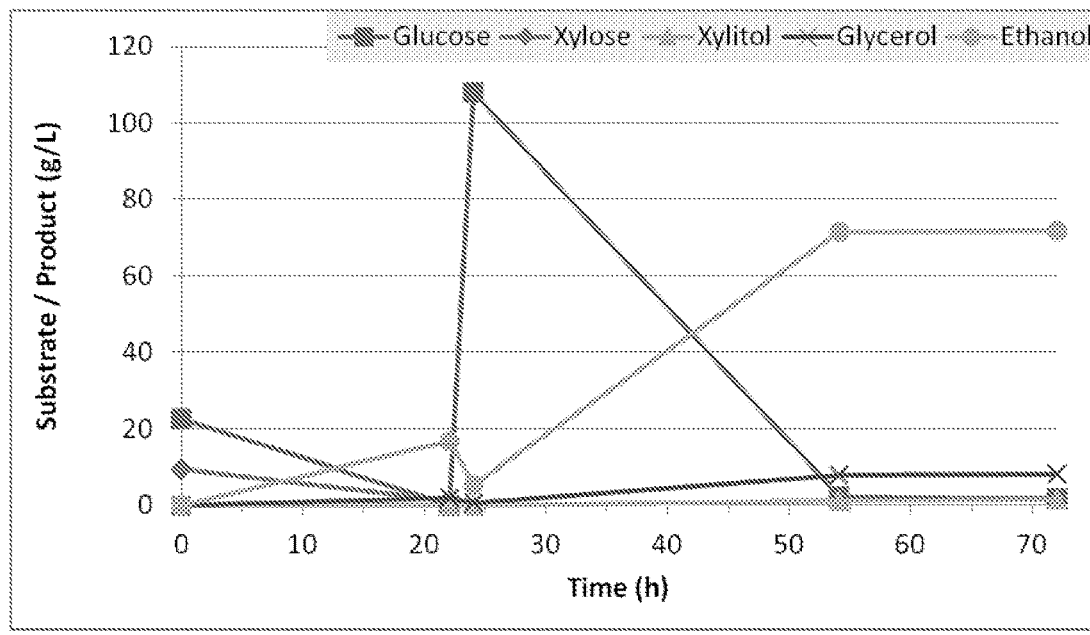
FIG. 11. Anaerobic fed-batch fermentation of glucose and xylose with a strain of the invention using Taurus13 in corn stover hydrolysate at pH 5.5. Glucose and xylose fermentation completed at 24 h, the medium also contains 1.7 g/L acetate. At 24.5 h, 108 g/L glucose is added and this feed increases the volume by 67%, the added glucose is fermented completely within 30 h. There is 8.3 g/L glycerol at the end of the fermentation, corresponding to a by-product formation of 6% of the fermented glucose.
Figure 12:
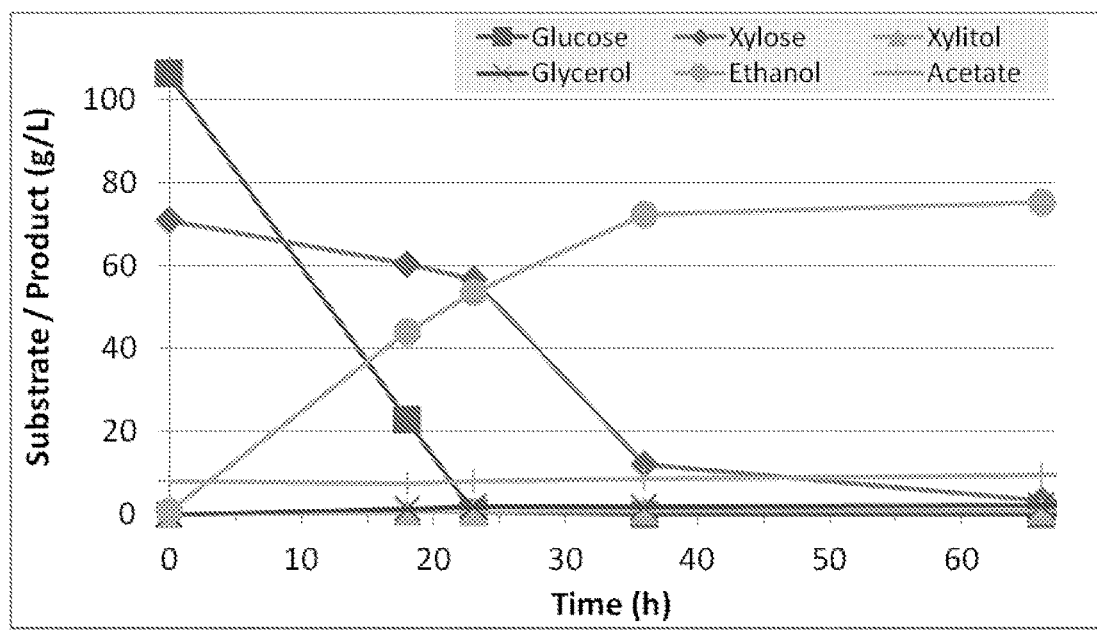
FIG. 12. Anaerobic fermentation of glucose and xylose with a strain of the invention using Taurus13 in minimal defined medium at pH 6. Glucose fermentation is completed at 20 h, and xylose is completely fermented after 40 hours, the medium also contains 8 g/L acetate. There is 2 g/L glycerol and 0.7 g/L xylitol at the end of the fermentation, corresponding to a by-product formation of <1.2% of the fermented sugars.
Figure 13:
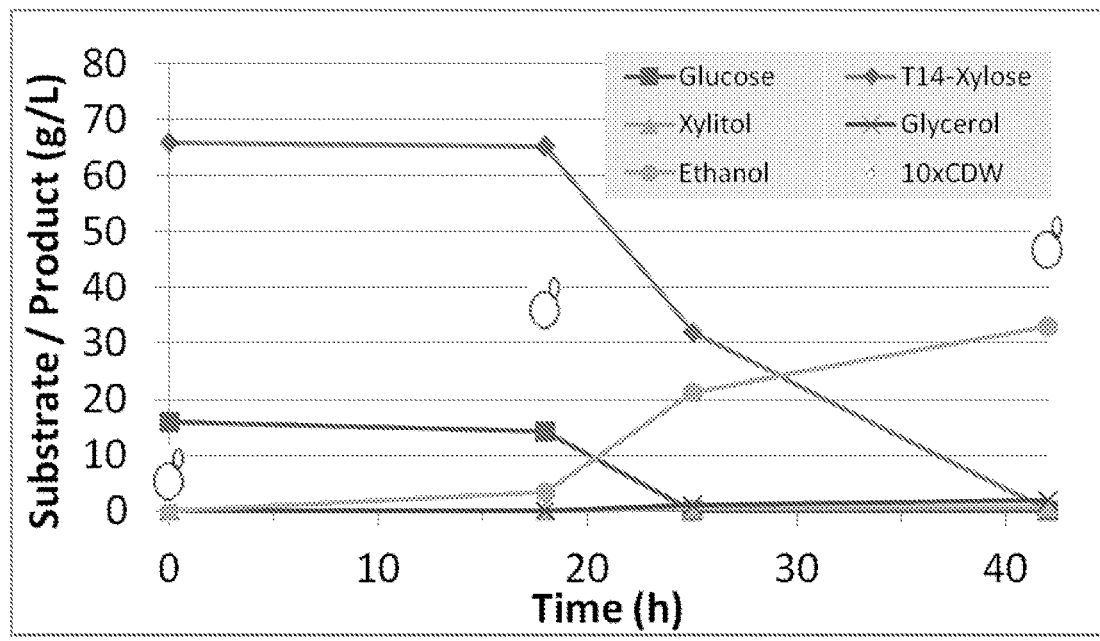
FIGS. 13-16. Anaerobic fermentation in defined minimal medium with a strain of the invention: The figures and strains are as follows: Taurus14 in FIG. 13; Taurus15 in FIG. 14; Taurus16 in FIG. 15; Taurus17 in FIG. 16. The glucose and xylose are fermented within 25 hours. There is minimal formation of by-products xylitol and glycerol (g/L), constituting <3% of the g/L fermented sugars. The cell dry weight (CDW, g/L is shown as circles×10) is at the start and end of the fermentation 0.5 (±0.1) and 6.2 (±0.7), respectively.
Figure 14:
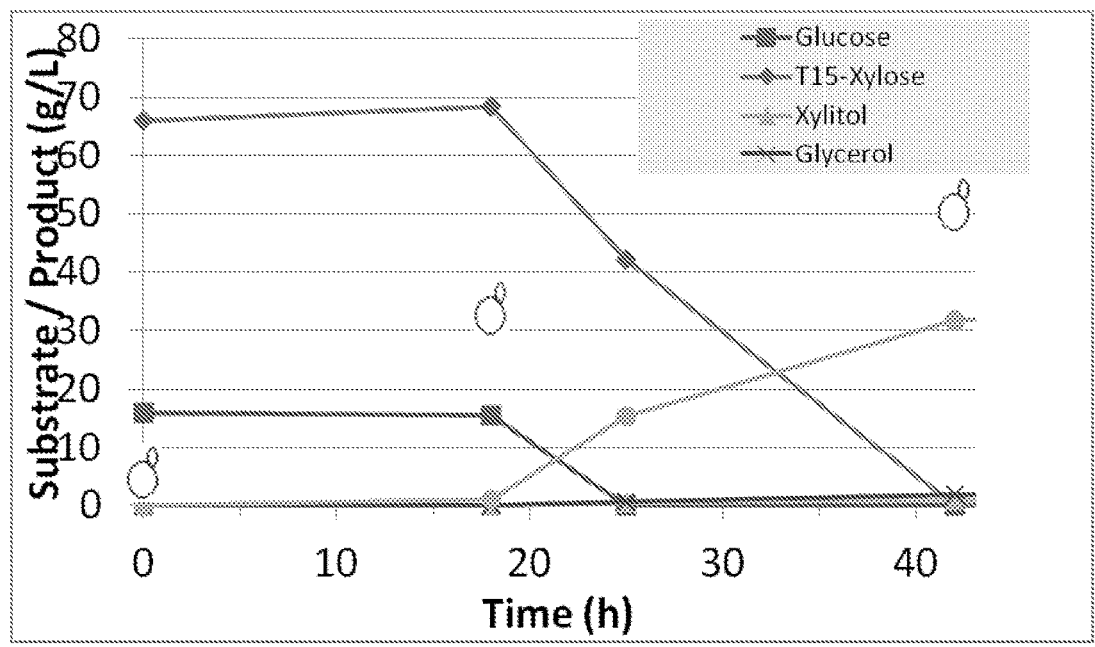
Figure 15:
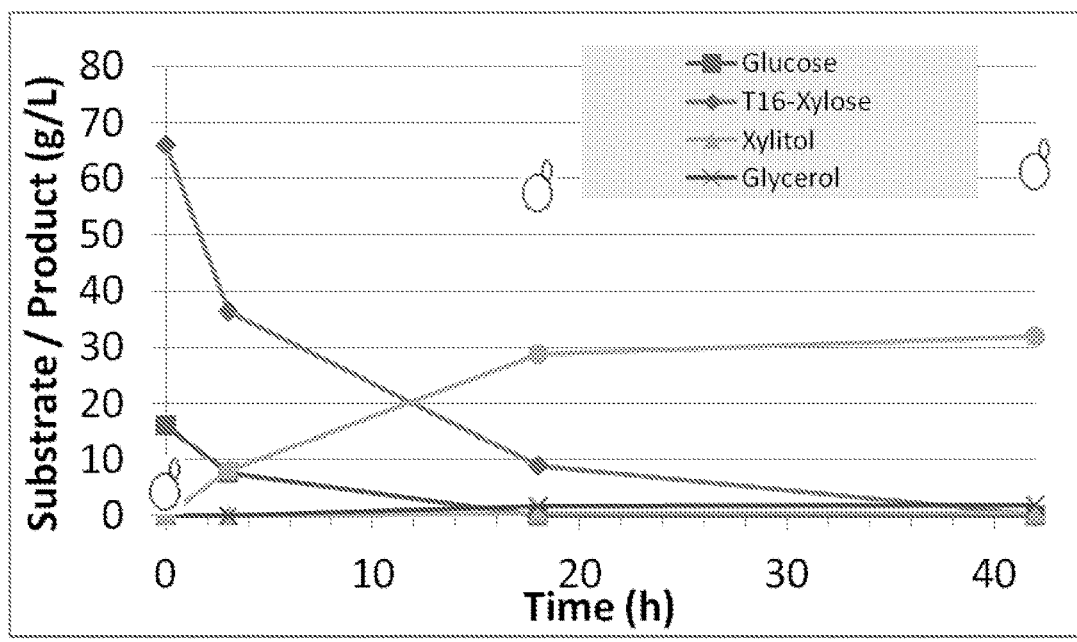
Figure 16:
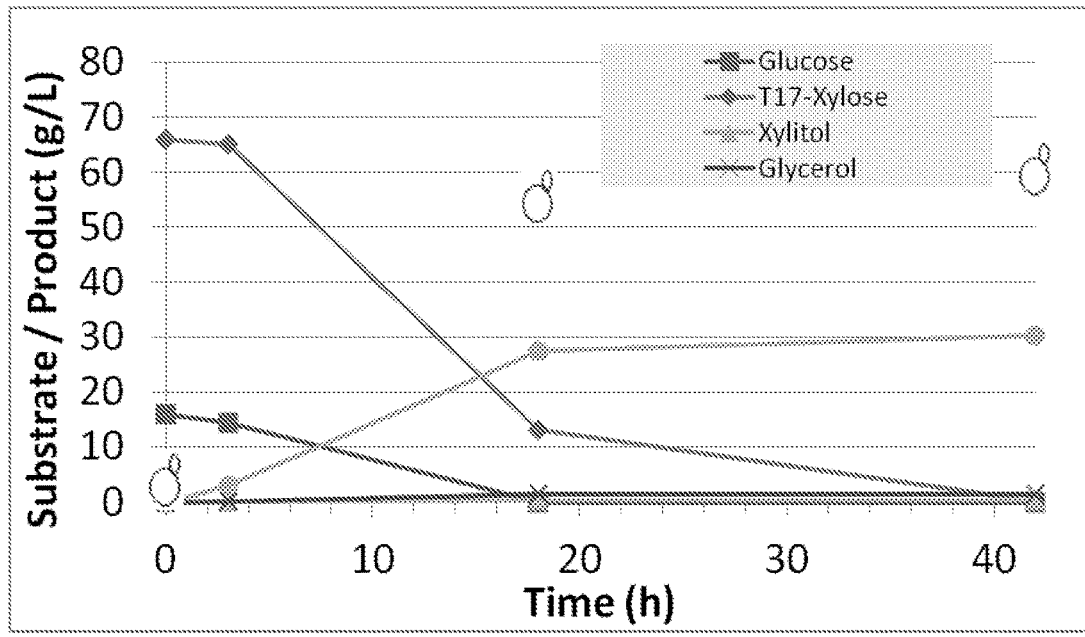
Figure 17:
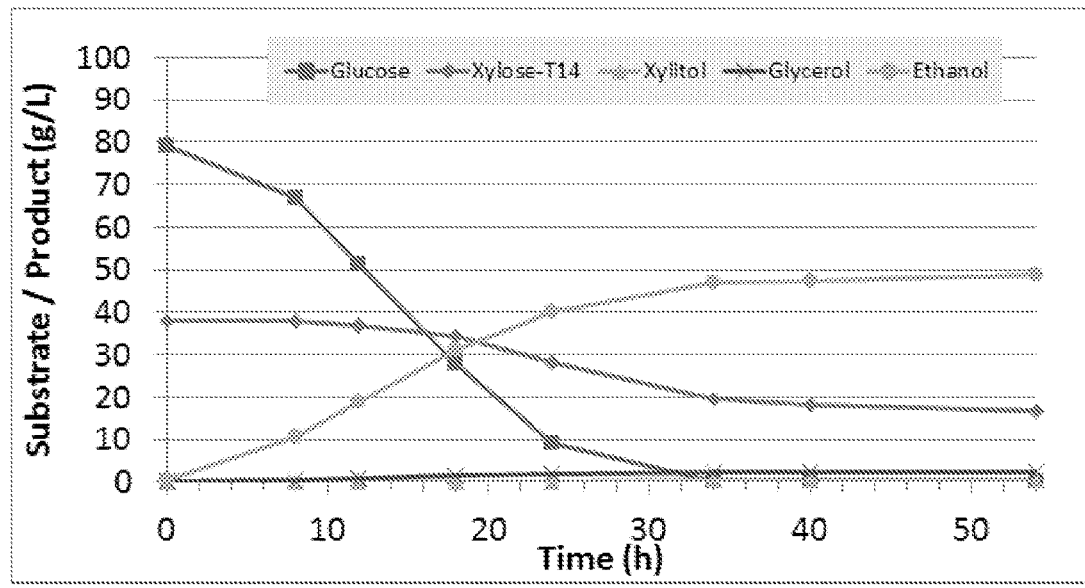
FIG. 17. Anaerobic fermentation of glucose and xylose with a strain of the invention using Taurus14 in corn stover hydrolysate at pH6. Glucose is fermented within 28 h and >90% xylose is fermented at 96 h. There is only 3 g/L glycerol and 0.6 g/L xylitol at the end of the fermentation, corresponding to very low by-product formation, <3% of the fermented sugar.
Figure 18:
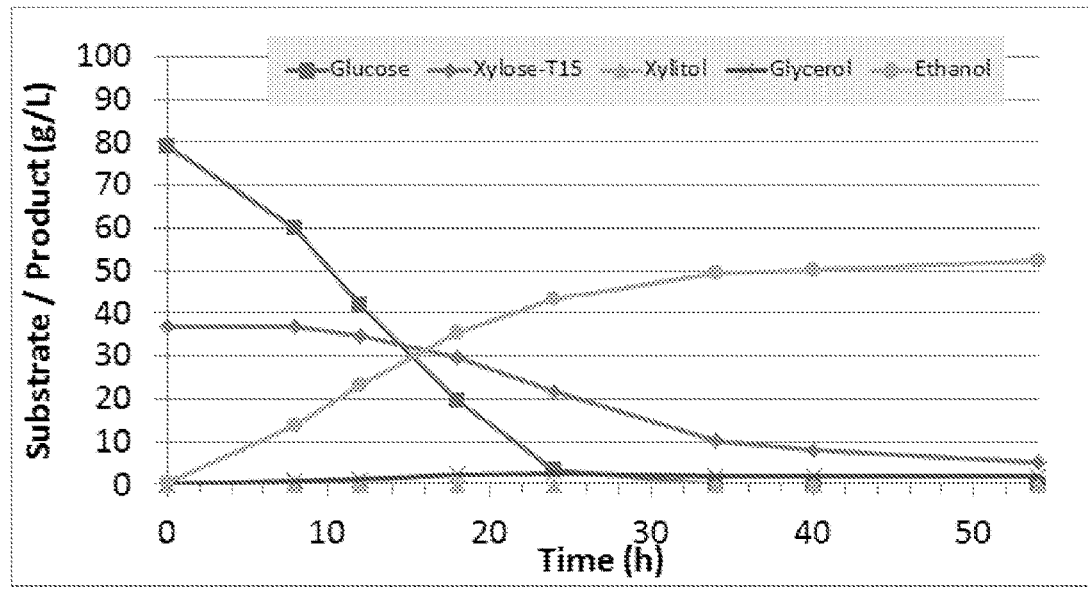
FIG. 18. Anaerobic fermentation of glucose and xylose with a strain of the invention using Taurus15 in corn stover hydrolysate at pH6. Glucose is fermented within 28 h and >90% xylose is fermented at 96 h. There is only 3 g/L glycerol and 0.1 g/L xylitol at the end of the fermentation, corresponding to very low by-product formation, <3% of the fermented sugar.
Figure 19:
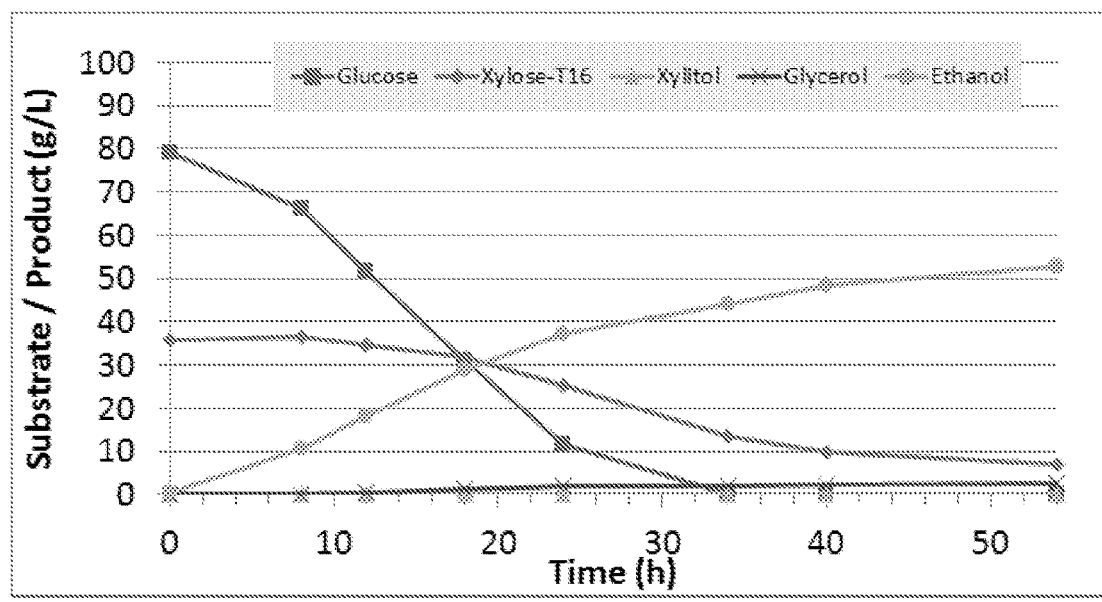
FIG. 19. Anaerobic fermentation of glucose and xylose with a strain of the invention using Taurus16 in corn stover hydrolysate at pH6. Glucose is fermented within 28 h and >90% xylose is fermented at 96 h. There is only 3 g/L glycerol and 0.1 g/L xylitol at the end of the fermentation, corresponding to very low by-product formation, <3% of the fermented sugar.
Figure 20:
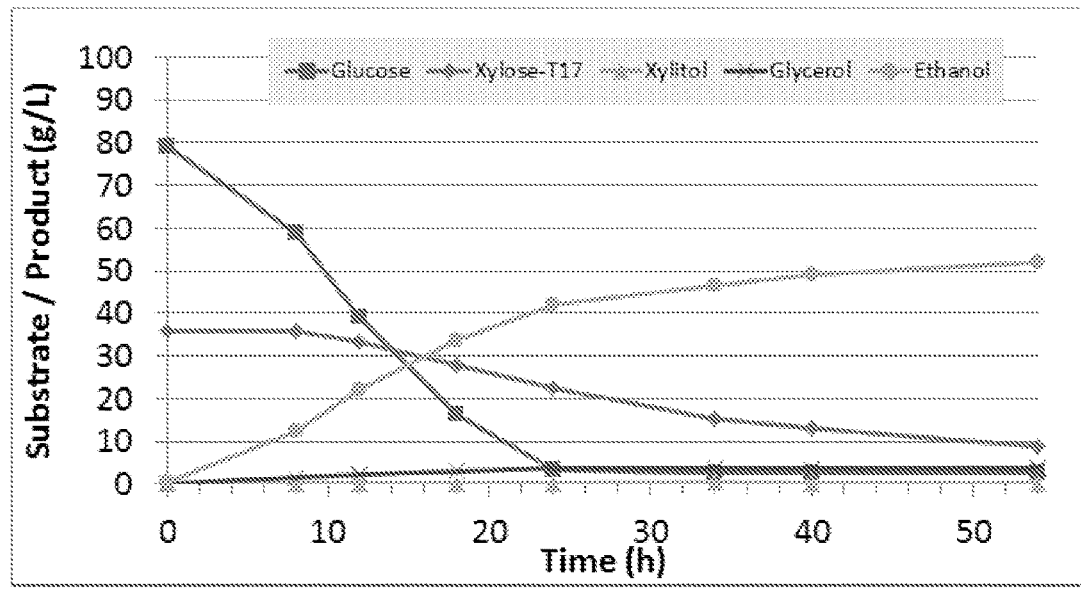
FIG. 20. Anaerobic fermentation of glucose and xylose with a strain of the invention using Taurus17 in corn stover hydrolysate at pH6. Glucose is fermented within 28 h and >90% xylose is fermented at 96 h. There is only 3.5 g/L glycerol and 0.2 g/L xylitol at the end of the fermentation, corresponding to very low by-product formation, <4% of the fermented sugar.
Figure 21:
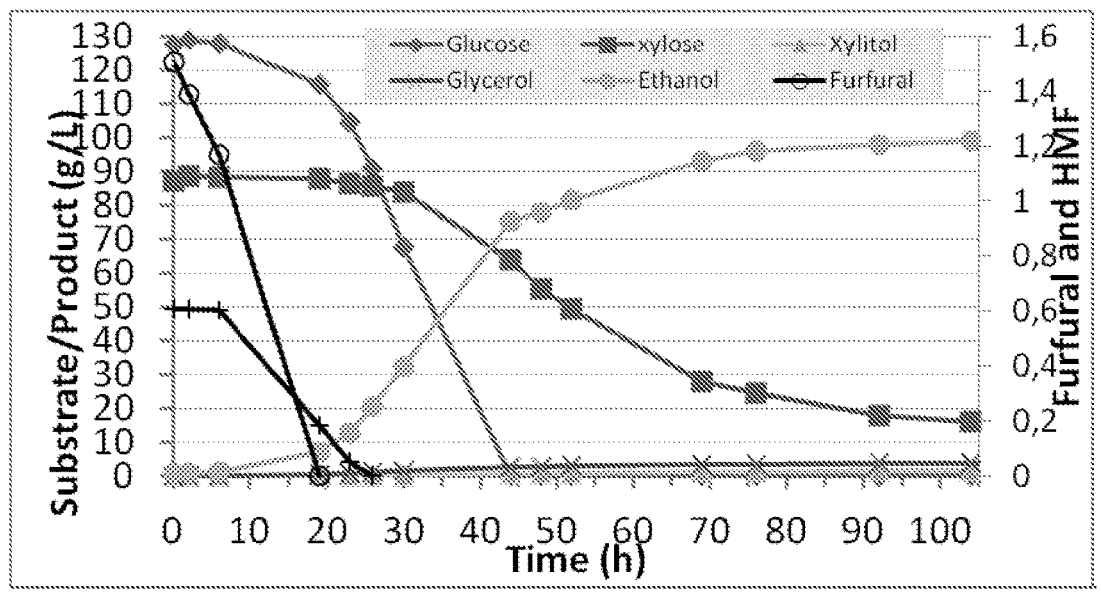
FIG. 21. Anaerobic fermentation of glucose and xylose with a strain of the invention using Taurus13 in corn cobs hydrolysate at pH5. Urea, $KH_2PO_4$ and $MgSO_4 \times 7H_2O$ have been added in the following amounts: 5, 6 and 1 g/L, respectively. Glucose is fermented within 40 h and most of the xylose is fermented at 96 h. There is only 3.5 g/L glycerol and 1.5 g/L xylitol at the end of the fermentation, corresponding to very low by-product formation, <2% of the fermented sugar.
Figure 22:
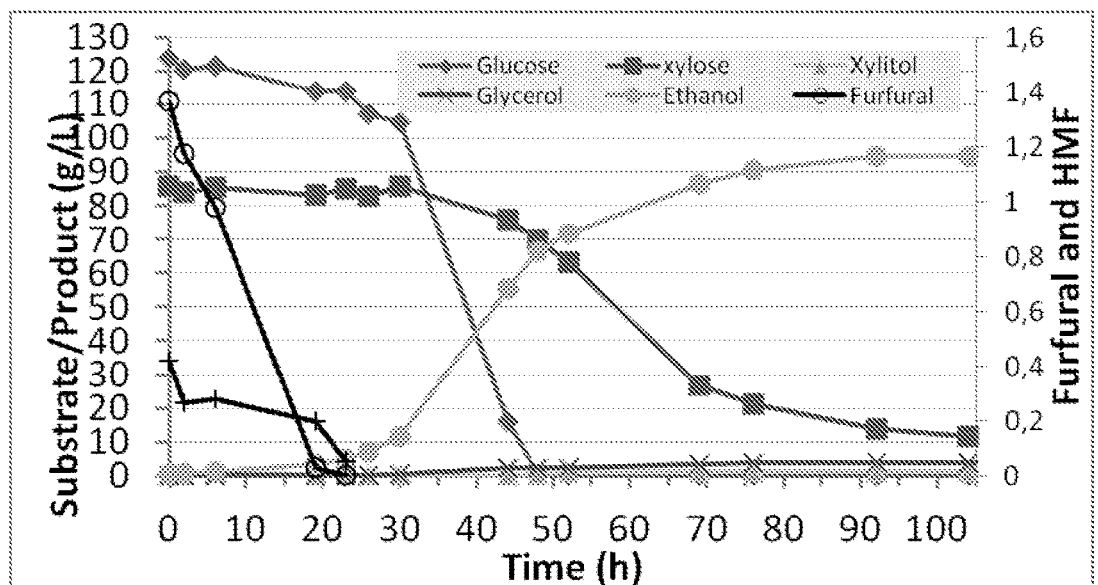
FIG. 22. Anaerobic fermentation of glucose and xylose with a strain of the invention using Taurus13 in Bagasse hydrolysate at pH5. Urea, $KH_2PO_4$ and $MgSO_4 \times 7H_2O$ have been added in the following amounts: 5, 6 and 1 g/L, respectively. Glucose is fermented within 45 h and most of the xylose is fermented at 96 h. There is only 3.5 g/L glycerol and 1.2 g/L xylitol at the end of the fermentation, corresponding to very low by-product formation, <2% of the fermented sugar FIG. 23. Anaerobic fermentation of glucose and xylose with a strain of the invention using Taurus13 in corn mash at pH5. Urea, $KH_2PO_4$ and $MgSO_4 \times 7H_2O$ have been added in the following amounts: 5, 6 and 1 g/L, respectively. Glucose and xylose is fermented within 30 h. There is only 11 g/L glycerol at the end of the fermentation.
Figure 25:
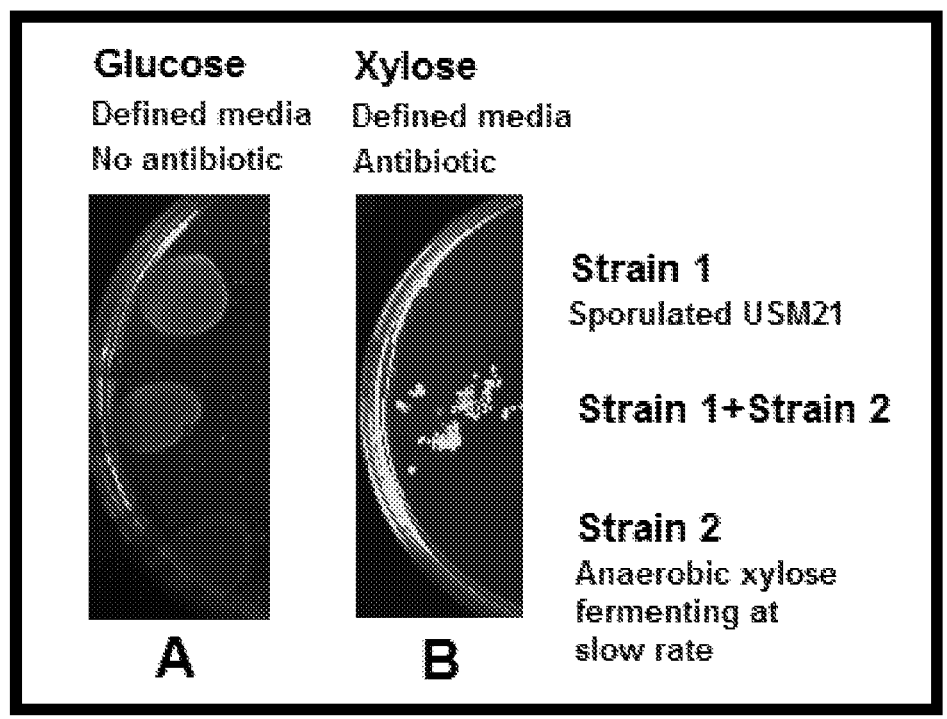
FIG. 25. Defined media plates with either glucose+No antibiotic (A) or xylose+antibiotic (B). The upper part is the sporulated USM21 strain (step a of the invention), while the lower part is the evolved xylose fermenting haploid strains that is able to perform slow xylose fermentation (step c of the invention). In the middle are sporulated USM21 strain mixed with the haploid xylose fermenting strain. After a few days of incubation at 30° C., plate A show that both cells types grow as expected on the glucose defined media plate. In (B) with xylose media USM21 strain is verfied not to be able to grow on xylose, while the haploid xylose fermenting strain is not able to cope with the toxcicity of the added antibiotic. Therefore is the designed method of this invention only allow for growth of the dipoild mated strain that gained beneficial traites from both strain, and hence this new strain cross grow on xylose in the presence of the antibiotic.

Day47: The cells in the micro aerobic chemostat were then grown anaerobically for 9 weeks using 15 g/L xylose defined medium, with feed rate of mu=0.12 $h^{-1}$, but with the pump turned off for 6 h then on for 6 h. The pH and temperature were maintained at pH5 and 33° C., respectively. The xylitol yield from consumed xylose was decreasing the first 35 Days and the feed continued for additional 30 Days (FIG. 2A). At Day65 the defined medium was mixed with hydrolysate leading to containing 30 g/L xylose+0.6 g/L glucose which was used for 34 Days and until the xylitol and glycerol yield <0.01 g per gram consumed xylose, see FIG. 2B. After Day75 constant feed was used. After 99 Days in the chemostat cells were streaked onto a YPD plate. Cells were streaked onto a YPD plate, and after 4 days at 30° C. one single colony was picked, and streaked onto a new YPD plate and again left at 4 days at 30° C. Then, single colony cells were used and grown over-night in defined medium with 3% glucose and cells frozen as glycerol stock and thereafter deposited and referred to as the respective strains Taurus 13, Taurus14, Taurus15, Taurus16 and Taurus17. Anaerobic fermentation using ligno-cellulose material is from the cells in a single colony on an YPD plate or from the cells stored as the 30% glycerol stock.

Experiment 2

Hydrolysates (pH): Hydrolysates (pH): wheat straw hydrolysate pH 5.0; Bagasse hydrolysate pH 5.0; birch hydrolysate pH 6.0; corn stover hydrolysate pH 5.0, hard wood hydrolysate pH 5.5; corn stover pH 5.5 fed-batch; SSF 10% WIS wheat straw pH5; SSF 10% WIS corn cobs pH5. Starch media (pH): Corn mash pH 5.0.

All hydrolysates were fermented anaerobically in FIGS. 4-23 without any substance additions besides a few drops of concentrated base/acid for setting the pH before adding the yeast. In FIGS. 17-23, 1 g/L each of Urea, $KH_2PO_4$, and corn steep liquor have been added to the corn stover.

Description of making agar plates, exemplified with a 2% xylose agar plate (0.5 L): Two separate flasks were autoclaved, 0.25 L with 15 g xylose and 0.25 L with 2.5 g $(NH4)_2SO_4$, 1.5 g $KH_2PO_4$, 0.25 g $MgSO_4$, 0.85 g Yeast nitrogen base and 10 g Agar. A stirrbar was included into one of the flask. After autoclavation, the flasks were set to cool at room-temperature for 10 min, the solutions were mixed in laf bench, stirred for 5 min, the plates were poured with 25 ml medium into each 90 mm diameter plate, the plates were left to solidify for 1 h. The plates were stored at 4° C. for up to 3 months.

Content description of plates used, following the same procedure as in the 2% xylose agar plate description, and autoclaving sugars separate. YPD agar plate: 20 g/L glucose, 20 g/L Bactopeptone, 10 g/L yeast extract, 20 g/L agar; 2% KAc agar plate: 20 g/L KAc, 20 g/L agar; 2% xylose agar plate: 20 g/L xylose, 1.3 g/L YNB, 5 g/L $(NH4)_2SO_4$, 3 g/L $KH_2PO_4$, 0.2 g/L $MgSO_4\times7H_2O$, 20 g/L agar.

Minimal medium with 15 g/L xylose (1 L): Autoclave in 2 flasks separately, 1 flask with 0.5 L $H_2O$ mixed with 15 g xylose, 1 flask with 5 g $(NH4)_2SO_4$, 3 g $KH_2PO_4$, 0.5 g $MgSO_4$ (Base salt). After autoclavation, the solutions were mixed and left to cool for 10 min and then adding 2 ml trace elements solution and 1 ml vitamin solution (Verdyun et al. Yeast, 8:501-517, 1992). Stock solution of 20× Base salt (1 L): 100 g/L $(NH4)_2SO_4$, 60 g/L $KH_2PO_4$, 4 g/L $MgSO_4\times7H_2O$.

Method Description for Anaerobic Fermentation

Day 1: Pre-culture: 50 µl yeast cells were taken frozen glycerol stock or single colony from YPD plate into 15 ml 30 g/L glucose and grown 24 h at 175 rpm and 30° C.

Day2: Culture to obtain yeast biomass: After 24 h and when $OD_{600}$=2-4, the 15 ml pre-culture was added to 150 ml of 30% filtered lignocellulose material pH6 with added 7.5 ml 20× base salt. Glucose and xylose was added from 400 g/L stock solutions to obtain 30 g/L glucose and 30 g/L xylose in the culture medium. The culture was left for 20 h at 130 rpm and 30° C.

Day 3: The cells in the shake flasks were transferred into pre-weighted bottles, and spun at 4000×g for 5 min. Cells from a 150 ml culture is enough for anaerobic fermentation of 4×50 ml with ligno cellulose using a CDW=2 g/L. After the centrifugation the medium was poured of and the remaining 1-2 ml of the residual liquid was removed with a micro-pipette. The bottle with the cell pellet was weighed, and the difference between empty and pellet containing centrifuge tube gave an estimate of the cell amount obtained.

Then 0.4 g wet cells were added to a volume of 50 ml into a 150 ml anaerobic flask with an airlock. The cultures in FIGS. 4-16 were incubated at 30° C. at 130 rpm for up to 25-72 hours when fermentation of glucose and xylose was completed. Samples were taken every third to $24^{th}$ hour for a total time of 72 hours. The results from cultures presented in FIG. 17-23 were incubated at 35° C. for a total time of 96 h. The sample was taken by suction out of the anaerobic chamber without opening up the airlock. The airlock glass cylinder was filled with 4 ml 30% glycerol solution during the fermentation.

Treatment of ligno cellulose liquid. The pH was set to a particular value pH 5, 5.5 or 6 using base addition. Then the solution was filtered using suction through 0.2 um nylon filter, it was then ready for the anaerobic fermentation experiment.

Sample collection and analysis: Samples were collected through-out the fermentations, each 0.5-1 ml liquid of sample was filtered through a 0.2 um nylon filter and then the solution was stored at −20° C. until collecting several samples for the HPLC analysis. In order to analyze samples, these were thawed at room temperature for 30 min, and for a 3× dilution was 0.2 ml sample was then mixed with 0.4 ml 5 mM $H_2SO_4$, before loading onto HPLC column. Some sample with high glucose/xylose (>70 g/L) and/or ethanol (>40 g/L) was a 6× dilution used, 0.1 ml sample was mixed with 0.5 ml 5 mM $H_2SO_4$. Analysis of sugars and metabolites were performed using a HPLC system (Ultimate 3000, Dionex, Sunnyvale, US). Glucose, xylose, ethanol, xylitol, glycerol, acetic acid, HMF and furfural were separated using an "RESEX ROA-Organic Acids H+(Phenomenex)" column (Bio-Rad Laboratories, München, Germany) with 5 mM $H_2SO_4$ as eluent. The column was operated at 80° C. and at a flow rate of 0.8 mL $min^{-1}$. Ethanol, xylitol, glycerol and acetic acid were detected with a refractive index detector Shodex RI-101 (Showa Denko, New York, N.Y.) while HMF and furfural were detected using an UV detector at 210 nm (Dionex, Sunnyvale, US).

Enzyme Assays

Xylose reductase activity was assayed at 37° C. in a reaction mixture containing 100 mM triethanolamine pH 7.0, 1.75 mM xylose, 10 mM NADPH and a suitable amount of cell-free extract. Xylitol dehydrogenase activity was assayed at 37° C. in a reaction mixture containing glycine/$MgCl_2$ 20/10 mM pH 9, 300 mM xylitol and 3 mM $NAD^+$ and a suitable amount of cell-free extract. The amount of xylitol or xylulose formed was determined monitoring at 340 nm from NADPH oxidation and NAD+ reduction, respectively (Bettiga et al., 2009, MCF, 8:40). Specific activity is expressed as units per mg protein. Protein was determined with the Bradford assay, with bovine γ-globulin as a standard. A unit (U) of xylose reductase activity is herein defined as the amount of enzyme producing 1 nmol of xylitol or xylulose per minute.

Method Description for Determining Amino Acid Sequence of modGre3.

The strains Taurus13, Taurus14, Taurus15, Taurus16, Taurus17 of this invention was streaked onto YPD-2% Glucose plates, then incubated in 30° C. for 3 days, a single colony from each strain was transferred into 15 ml minimal media 3% glucose and put at 200 rpm, 30° C. over-night. The next day was the cells spun down, and genomic DNA prepared. 10 ng of purified genomic DNA was then put in a 50 μl polymerase chain reaction, the modGre3 gene was amplified in a standard 30-cycle reaction with flanking primers. The amplified 1 kb PCR fragment DNA was purified and DNA sequencing using flanking primers. The modGre3 gene was identified in all of the said strains Taurus13, Taurus14, Taurus15, Taurus16, Taurus17.

The invention claimed is:

1. A strain of *Saccharomyces cerevisiae* selected from the group consisting of Taurus 13 having deposit number CBS137333, Taurus 14 having deposit number CBS 137663, Taurus 15 having deposit number CBS 137664, Taurus 16 having deposit number CBS 137665, and Taurus 17 having deposit number CBS 137666.

* * * * *